US012773540B2

(12) United States Patent
Campbell et al.

(10) Patent No.: US 12,773,540 B2
(45) Date of Patent: Oct. 27, 2026

(54) SYSTEMS, CATHETERS, AND METHODS FOR TREATING ALONG THE CENTRAL NERVOUS SYSTEM

(71) Applicant: PHAROAH NEURO, INC., Minneapolis, MN (US)

(72) Inventors: Susan Rosemary Campbell, White Bear Township, MN (US); Bejan Michael Darbandi, Chanhassen, MN (US); John Leonard Gohman, Minneapolis, MN (US); Blake Anthony Hedstrom, Minneapolis, MN (US); Jack Michael Mondry, Edina, MN (US)

(73) Assignee: PHARAOH NEURO, INC.

( * ) Notice: Subject to any disclaimer, the term of this patent is extended or adjusted under 35 U.S.C. 154(b) by 332 days.

(21) Appl. No.: 18/645,549

(22) Filed: Apr. 25, 2024

(65) Prior Publication Data

US 2024/0293649 A1 Sep. 5, 2024

Related U.S. Application Data

(63) Continuation of application No. 16/460,090, filed on Jul. 2, 2019, now Pat. No. 11,992,637.

(Continued)

(51) Int. Cl.
*A61M 27/00* (2006.01)
*A61M 1/00* (2006.01)

(52) U.S. Cl.
CPC ............ *A61M 27/006* (2013.01); *A61M 1/74* (2021.05); *A61M 1/88* (2021.05); *A61M 2205/3334* (2013.01); *A61M 2205/3355* (2013.01)

(58) Field of Classification Search
CPC .......... A61M 1/74; A61M 1/88; A61M 27/00; A61M 27/006; A61M 2202/0464; A61M 2250/3331; A61M 2250/3334
See application file for complete search history.

(56) References Cited

U.S. PATENT DOCUMENTS 7,025,742 B2 4/2006 Rubenstein et al.
7,909,790 B2 3/2011 Burnett
(Continued)

FOREIGN PATENT DOCUMENTS

JP 2004344299 A 12/2004
JP 2006314346 A 11/2006
(Continued)

OTHER PUBLICATIONS

International Search Report and Written Opinion dated Oct. 24, 2019, for International Application No. PCT/US2019/040285.
(Continued)

*Primary Examiner* — Philip R Wiest
(74) *Attorney, Agent, or Firm* — Seager, Tufte & Wickhem LLP

(57) ABSTRACT

Systems, catheters, and methods for accessing and treating along the central nervous system are disclosed. An example method may control operation of a pump of pump/filtration system to facilitate removing cerebrospinal fluid from a patient, filtering the cerebrospinal fluid with a filter module to remove waste product, and returning the filtered cerebrospinal fluid to the patient. Operation of the pump may be adjusted based on a value related to a measure sensed by a sensor in communication with a lumen carrying cerebrospinal fluid through the filtration system.

20 Claims, 8 Drawing Sheets

Related U.S. Application Data

(60) Provisional application No. 62/693,225, filed on Jul. 2, 2018.

(56) References Cited

U.S. PATENT DOCUMENTS

| | | | | |
|---|---|---|---|---|
| 8,398,577 | B2 * | 3/2013 | Burnett ............... | A61M 27/002 604/9 |
| 8,435,204 | B2 | 5/2013 | Lad et al. | |
| 11,992,637 | B2 * | 5/2024 | Campbell ............... | A61M 1/74 |
| 2005/0145009 | A1 | 7/2005 | Vanderveen et al. | |
| 2012/0302938 | A1 * | 11/2012 | Browd ................ | A61M 39/284 604/9 |
| 2015/0094644 | A1 * | 4/2015 | Lenihan ................ | A61M 39/24 604/9 |
| 2016/0051801 | A1 | 2/2016 | Vase | |
| 2017/0035950 | A1 * | 2/2017 | Meyering ............. | A61M 1/884 |
| 2017/0035998 | A1 | 2/2017 | Meyering et al. | |

FOREIGN PATENT DOCUMENTS

| | | | |
|---|---|---|---|
| WO | 2010123558 | A1 | 10/2010 |
| WO | 2017023419 | A1 | 2/2017 |

OTHER PUBLICATIONS

Extended European Search Report and Search Opinion received for EP Application No. 25177734.8, mailed on Sep. 10, 2025, 14 pages.

* cited by examiner

350

| Description | Name | Zone 0 | Zone 1 | Zone 2 | Zone 3 | Zone 4 | Zone 5 | |
|---|---|---|---|---|---|---|---|---|
| Change in Filter Pressure (mmHg/5min) | Delta-FP Range | <=5 | > 5 <=10 | > 10 <=20 | > 20 <=25 | > 25 <=30 | > 30 | 352 |
| Filter Pressure Min (mmHg) | FP-Min | 50 | 50 | 50 | 50 | 50 | 50 | 354 |
| Filter Pressure Max (mmHg) | FP-Max | 200 | 190 | 180 | 170 | 160 | 50 | 356 |
| Small Increase in Pump Rate (ml/min) | SmStepUp | 0.01 | 0.01 | 0.01 | 0.01 | 0.01 | 0 | 358 |
| Large Increase in Pump Rate (ml/min) | LgStepUp | 0.01 | 0 | 0 | 0 | 0 | 0 | 360 |
| Decrease in Pump Rate (ml/min, %) | StepDown | 0.01 | 5% | 10% | 20% | 25% | 50% | 362 |
| Increase Period (seconds) | UpTimer | 60 | 60 | 60 | 60 | 60 | 60 | 364 |
| Decrease Period (seconds) | DownTimer | 60 | 60 | 60 | 60 | 60 | 30 | 366 |

FIG. 6

SYSTEMS, CATHETERS, AND METHODS FOR TREATING ALONG THE CENTRAL NERVOUS SYSTEM

CROSS-REFERENCE TO RELATED APPLICATIONS

This application is a continuation of U.S. application Ser. No. 16/460,090, filed Jul. 2, 2019, which claims the benefit of priority under 35 U.S.C. § 119 to U.S. Provisional Application Ser. No. 62/693,225 filed Jul. 2, 2018, the entirety of which is incorporated herein by reference.

TECHNICAL FIELD

The present disclosure relates to systems, catheters, and methods for treating along the central nervous system.

BACKGROUND

A wide variety of medical devices have been developed for medical use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example 1. A cerebrospinal fluid flow control system is disclosed. The system may include a pump configured to pump cerebrospinal fluid along a fluid circuit, a fluid line in communication with the pump, the fluid line having an inlet configured to receive cerebrospinal fluid from a patient, an outlet configured to provide conditioned cerebrospinal fluid to the patient, and a lumen configured to facilitate travel of cerebrospinal fluid along the fluid circuit from the inlet of the fluid line to the pump and from the pump to the outlet of the fluid line, a sensor in communication with the lumen of the fluid line, the sensor is configured to sense a measure related to a pressure in the lumen of the fluid line at a location downstream of the pump, a controller in communication with the sensor and the pump. The controller may be configured to control operation of the pump based on the measure sensed by the sensor.

Alternatively or additionally to any of the embodiments above, the controller may be configured to control operation of the pump based on a delta value based on the measure sensed by the sensor, the delta value is a difference between a value based on the measure sensed by the sensor at a time T and a value based on the measure sensed by the sensor at a previous time of the time *T minus* a time interval N.

Alternatively or additionally to any of the embodiments above, the time interval N may be equal to five minutes.

Alternatively or additionally to any of the embodiments above, controller may be configured to control operation of the pump according to a first control protocol when the value based on the measure sensed by the sensor at time T has not reached a threshold value, and a second control protocol when the value based on the measure sensed by the sensor at time T has reached or gone beyond the threshold value, the second control protocol is different than the first control protocol.

Alternatively or additionally to any of the embodiments above, the controller may be configured to determine the threshold value based on the delta value.

Alternatively or additionally to any of the embodiments above, the controller may be configured to adjust the threshold value based on a length of continuous time the pump has been operating.

Alternatively or additionally to any of the embodiments above, the controller may be configured such that when controlling operation of the pump according to the first control protocol, the threshold value is a first threshold value and the controller compares the value based on the measure sensed by the sensor to a second threshold value, the second threshold value is based on the delta value. When the value based on the measure sensed by the sensor has not reached or gone beyond the second threshold value, the controller may increase a pumping rate of the pump by a first predetermined amount. When the value based on the measure sensed by the sensor has reached or gone beyond the second threshold value, the controller may increase the pumping rate of the pump by a second predetermined amount.

Alternatively or additionally to any of the embodiments above, the first predetermined amount and the second predetermined amount may be based on the delta value.

Alternatively or additionally to any of the embodiments above, the system may include a timer timing an amount of time the controller has been controlling operation of the pump according to the first control protocol, and when the controller increases the pumping rate of the pump one of the first predetermined amount and the second predetermined amount and the increase in the pumping rate is equal to or less than zero, the controller may be configured to stop the timer and re-calculate the delta value.

Alternatively or additionally to any of the embodiments above, when the controller increases the pumping rate of the pump one of the first predetermined amount and the second predetermined amount and the increase in the pumping rate is greater than zero, the controller may be configured to determine whether the timer is running, and when the controller determines the timer is not running, the controller is configured to start the timer and recalculate the delta value.

Alternatively or additionally to any of the embodiments above, when the controller determines the timer is running, the controller may be configured to determine whether the timer has expired; when the controller determines the timer has not expired, the controller may be configured to recalculate the delta value; and when the controller determines the timer has expired, the controller is configured to increase the pumping rate by one of the first predetermined amount and the second predetermined amount based on whether the value based on the measure sensed by the sensor has or has not reached or gone beyond the second threshold value.

Alternatively or additionally to any of the embodiments above, the timer may be a first timer and the system may further include a second timer; when controlling operation of the pump according to the second control protocol, the second timer is configured to time an amount of time the controller has been controlling operation of the pump according to the second control protocol; the controller may determine whether the second timer is running; and when the controller determines the second timer is not running, the controller may be configured to start the second timer and recalculate the delta value.

Alternatively or additionally to any of the embodiments above, when the controller determines the second timer is running, the controller may be configured to determine whether the second timer has expired; when the controller determines the second timer has not expired, the controller may be configured to recalculate the delta value; and when the controller determines the second timer has expired, the controller may be configured to decrease the pumping rate by a third predetermined amount.

Alternatively or additionally to any of the embodiments above, when the controller determines the second timer has expired, the controller may be configured to restart the second timer.

Alternatively or additionally to any of the embodiments above, the controller may be configured to recalculate the delta value after restarting the second timer.

Alternatively or additionally to any of the embodiments above, the controller may be configured to determine the third predetermined amount based on the delta value.

Alternatively or additionally to any of the embodiments above, the third predetermined amount is a percentage value of the pumping rate of the pump.

Alternatively or additionally to any of the embodiments above, the system may further include a timer and when controlling operation of the pump according to the second control protocol, the timer may be configured to time an amount of time the controller has been controlling operation of the pump according to the second control protocol; the controller determines whether the timer is running; and when the controller determines the timer is not running, the controller may be configured to start the timer and recalculate the delta value.

Alternatively or additionally to any of the embodiments above, when the controller determines the timer is running, the controller is configured to determine whether the timer has expired; when the controller determines the timer has not expired, the controller may be configured to recalculate the delta value; and when the controller determines the timer has expired, the controller may be configured to decrease a pumping rate of the pump by a predetermined amount.

Alternatively or additionally to any of the embodiments above, when the controller determines the timer has expired, the controller may be configured to restart the timer.

Alternatively or additionally to any of the embodiments above, the controller may be configured to recalculate the delta value after restarting the timer.

Alternatively or additionally to any of the embodiments above, the controller may be configured to operate the pump according to a zone of operation based on the delta value.

Alternatively or additionally to any of the embodiments above, the controller may be configured to control a pumping rate of the pump based on the zone of operation and values in a look-up table.

Alternatively or additionally to any of the embodiments above, the system may further comprise a filter module configured to receive cerebrospinal fluid from the lumen of the fluid line at a location downstream of the sensor.

Alternatively or additionally to any of the embodiments above, the filter module may comprises one or more tangential flow filters.

Alternatively or additionally to any of the embodiments above, the filter module may comprise a first filter configured to output a first output of conditioned cerebrospinal fluid and output initial waste fluid, and a second filter downstream of the first filter, the second filter configured to receive the initial waste fluid, output a second output of conditioned cerebrospinal fluid, and output a final waste fluid.

Alternatively or additionally to any of the embodiments above, the system may further comprise a waste pump in communication with the fluid line and located downstream of the second filter, and the waste pump may be configured to at least partially control a waste pumping rate at which the final waste fluid is outputted from the second filter.

Alternatively or additionally to any of the embodiments above, the system may further comprise a waste pump in communication with the fluid line and located downstream of the filter module, and the waste pump may be configured to at least partially control a waste pumping rate at which waste fluid is outputted from the filter module.

Alternatively or additionally to any of the embodiments above, the fluid line may comprise a plurality of tubular components configured to facilitate maintaining a desired pressure within the fluid circuit.

A cerebrospinal fluid conditioning system is disclosed. The system may comprise a pump having a pumping rate and configured to pump cerebrospinal fluid along a fluid circuit, a filter module configured to receive cerebrospinal fluid pumped along the fluid circuit, a fluid line in communication with the pump, the fluid line may have an inlet configured to receive cerebrospinal fluid from a patient, an outlet configured to provide filtered cerebrospinal fluid to the patient from the filter module, and a lumen configured to facilitate travel of cerebrospinal fluid along the fluid circuit from the inlet of the fluid line to the filter module and from the filter module to the outlet of the fluid line, a filter pressure sensor in communication with the lumen of the fluid line at a location upstream of the filter module, the filter pressure sensor is configured to sense a measure related to a pressure in the lumen of the fluid line at the location upstream of the filter module, a controller in communication with the filter pressure sensor and the pump, and the controller may be configured to control operation of the pump based on one or both of a value based on the measure sensed by the filter pressure sensor and a delta value calculated by the controller, the delta value is a difference between the value based on the measure sensed by the filter pressure sensor at a time T and the value based on the measure sensed by the filter pressure sensor at a previous time of the time *T minus* a time interval N.

Alternatively or additionally to any of the embodiments above, the filter module may comprise a first filter configured to output a first output of filtered cerebrospinal fluid and output initial waste fluid, and a second filter downstream of the first filter, the second filter configured to receive the initial waste fluid, output a second output of filtered cerebrospinal fluid, and output a final waste fluid.

Alternatively or additionally to any of the embodiments above, the filter module may comprise a first tangential flow filter and a second tangential flow filter, the second tangential flow filter may be positioned along the fluid line at a location downstream of the first tangential flow filter.

Alternatively or additionally to any of the embodiments above, the system may further comprise a waste pump in communication with the fluid line and located downstream of the filter module, and the waste pump may be configured to at least partially control a waste pumping rate at which waste fluid is outputted from the fluid line.

Alternatively or additionally to any of the embodiments above, the pump may be positioned along the fluid line at a location upstream of the filter module.

Alternatively or additionally to any of the embodiments above, the location upstream of the filter module at which the filter pressure sensor is in communication with the lumen of the fluid line may be downstream of the pump.

Alternatively or additionally to any of the embodiments above, the system may further comprise an inlet pressure sensor in communication with the controller and the lumen of the fluid line at a location upstream of the pump and the filter module; and the controller may be configured to shut down the pump when a value based on the measure sensed by the inlet pressure sensor has reached or gone beyond a predetermined threshold.

Alternatively or additionally to any of the embodiments above, the system may further comprise an outlet pressure sensor in communication with the controller and the lumen of the fluid line at a location downstream of the pump and the filter module, and the controller may be configured to shut down the pump when a value based on the measure sensed by the outlet pressure sensor has reached or gone beyond a predetermined threshold.

Alternatively or additionally to any of the embodiments above, the controller may be configured to control operation of the pump according to a first control protocol when the value based on the measure sensed by the filter pressure sensor at time T has not reached a threshold value, and according to a second control protocol when the value based on the measure sensed by the filter pressure sensor at time T has reached or gone beyond the threshold value, the second control protocol may be different than the first control protocol.

Alternatively or additionally to any of the embodiments above, the controller may be configured such that when controlling operation of the pump according to the first control protocol, the threshold value may be a first threshold value and the controller may: compare the value based on the measure sensed by the filter pressure sensor to a second threshold value, the second threshold value may be based on the delta value; when the value based on the measure sensed by the filter pressure sensor has not reached or gone beyond the second threshold value, the controller may increase a pumping rate of the pump by a first predetermined amount; and when the value based on the measure sensed by the filter pressure sensor has reached or gone beyond the second threshold value, the controller may increase the pumping rate of the pump by a second predetermined amount.

Alternatively or additionally to any of the embodiments above, the system may further comprise a timer timing an amount of time the controller has been controlling operation of the pump according to the first control protocol; and when the controller increases the pumping rate of the pump by one of the first predetermined amount and the second predetermined amount and the increase in the pumping rate is equal to or less than zero, the controller may be configured to stop the timer and re-calculate the delta value.

Alternatively or additionally to any of the embodiments above, when the controller increases the pumping rate of the pump by one of the first predetermined amount and the second predetermined amount and the increase in the pumping rate is greater than zero, the controller may be configured to: determine whether the timer is running; and when the controller determines the timer is not running, the controller may be configured to start the timer and recalculate the delta value.

Alternatively or additionally to any of the embodiments above, when the controller determines the timer is running, the controller may be configured to determine whether the timer has expired; when the controller determines the timer has not expired, the controller may be configured to recalculate the delta value; and when the controller determines the timer has expired, the controller may be configured to increase the pumping rate by one of the first predetermined amount and the second predetermined amount based on whether the value based on the measure sensed by the filter pressure sensor has or has not reached or gone beyond the second threshold value.

Alternatively or additionally to any of the embodiments above, the timer may be a first timer and the system further includes a second timer; when controlling operation of the pump according to the second control protocol, the second timer may be configured to time an amount of time the controller has been controlling operation of the pump according to the second control protocol; the controller may determine whether the second timer is running; and when the controller determines the second timer is not running, the controller may be configured to start the second timer and recalculate the delta value.

Alternatively or additionally to any of the embodiments above, when the controller determines the second timer is running, the controller may be configured to determine whether the second timer has expired; when the controller determines the second timer has not expired, the controller may be configured to recalculate the delta value; and when the controller determines the second timer has expired, the controller may be configured to decrease the pumping rate by a third predetermined amount.

Alternatively or additionally to any of the embodiments above, the third predetermined amount may be a percentage value of the pumping rate of the pump.

Alternatively or additionally to any of the embodiments above, when the controller determines the second timer has expired, the controller may be configured to restart the second timer.

Alternatively or additionally to any of the embodiments above, the controller may be configured to recalculate the delta value after restarting the second timer.

A method of controlling cerebrospinal fluid flow through a cerebrospinal fluid filtering module is disclosed. The method may comprise pumping cerebrospinal fluid through a filter module with a pump at a pumping rate via a fluid line, the fluid line having an inlet configured to receive cerebrospinal fluid from a patient, an outlet configured to provide filtered cerebrospinal fluid to the patient from the filter module, and a lumen configured to facilitate travel of cerebrospinal fluid from the inlet of the fluid line to the filter module and from the filter module to the outlet of the fluid line, sensing a measure related to a pressure in the lumen of the fluid line at a location upstream of the filter module; and controlling operation of the pump in an automated manner based on one or both of a value based on the measure related to a pressure in the lumen of the fluid line sensed at a location upstream of the filter module and a delta value, the delta value is a difference between the value based on the measure related to a pressure in the lumen of the fluid line at a location upstream of the filter module at a time T and the value based on the measure related to a pressure in the lumen of the fluid line sensed at a location upstream of the filter module at a previous time of the time *T minus* a time interval N.

Alternatively or additionally to any of the embodiments above, controlling operation of the pump in an automated matter may comprise controlling operation of the pump according to a first control protocol when the value based on the measure related to a pressure in the lumen of the fluid line at the time T has not reached a threshold; and controlling operation of the pump according to a second control protocol when the value based on the measure related to a pressure in the lumen of the fluid line at the time T has reached or gone beyond the threshold, the first control protocol is different than the second control protocol.

Alternatively or additionally to any of the embodiments above, the method may further comprise determine in an automated manner the threshold based on the delta value.

Alternatively or additionally to any of the embodiments above, the method may further comprise adjusting the threshold in an automated manner based on a length of continuous time the pump has been operating.

Alternatively or additionally to any of the embodiments above, when controlling operation of the pump according to the first control protocol, the threshold may be a first threshold value and the method may further comprise comparing the value based on the measure related to a pressure in the lumen of the fluid line at the time T to a second threshold value, the second threshold value is based on the delta value; when the value based on the measure related to a pressure in the lumen of the fluid line at the time T has not reached or gone beyond the second threshold value, increasing a pumping rate of the pump by a first predetermined amount; and when the value based on the measure related to a pressure in the lumen of the fluid line at the time T has reached or gone beyond the second threshold value, increasing the pumping rate of the pump by a second predetermined amount.

Alternatively or additionally to any of the embodiments above, the method may further comprise determining in an automated manner the first predetermined amount and the second predetermined amount based on the delta value.

Alternatively or additionally to any of the embodiments above, the method may further comprise timing in an automated manner with a timer an amount of time the pump has been controlled according to the first control protocol; and when pumping rate of the pump has been increased by one of the first predetermined amount and the second predetermined amount and the increase in the pumping rate is equal to or less than zero, stopping the timing of the amount of time the pump has been controlled according to the first control protocol and recalculating the delta value Alternatively or additionally to any of the embodiments above, when the pumping rate of the pump has been increased by one of the first predetermined amount and the second predetermined amount and the increase in the pumping rate is greater than zero, the method may further comprise determining whether the timer is running; and starting the timer and recalculating the delta value when the timer is determined to be not running.

Alternatively or additionally to any of the embodiments above, the method may further comprise determining whether the timer has expired; when it is determined the timer has expired, recalculating the delta value; and when it is determined the timer has expired, increasing the pumping rate by one of the first predetermined amount and the second predetermined amount based on whether the value based on the measure related to a pressure in the lumen of the fluid line at the time T has or has not reached or gone beyond the second threshold value.

Alternatively or additionally to any of the embodiments above, the timer may be a first timer and the method may further comprise timing with a second timer an amount of time the pump has been controlled according to the second control protocol; determining whether the second timer is running, the second timer is configured to time an amount of time the pump has been controlled according to the second control protocol; and starting the second timer and recalculating the delta value when the second timer is determined to be not running.

Alternatively or additionally to any of the embodiments above, the method may further comprise determining whether the second timer has expired after the second timer has been determined to be running; recalculating the delta value when the second timer has been determined to not have expired; and when it has been determined the second timer has expired, decreasing the pumping rate by a third predetermined amount.

Alternatively or additionally to any of the embodiments above, the method may further comprise restarting the second timer when second timer has been determined to have expired.

Alternatively or additionally to any of the embodiments above, the method may further comprise recalculating the delta value after restarting the second timer.

Alternatively or additionally to any of the embodiments above, the method may further comprise determining the third predetermined amount based on the delta value.

Alternatively or additionally to any of the embodiments above, the method may further comprise determining the third predetermined amount based on a percentage value of the pumping rate of the pump.

Alternatively or additionally to any of the embodiments above, when controlling operation of the pump according to the second control protocol, the method may further comprise determining whether a timer is currently timing an amount of time the pump has been controlled according to the second control protocol; and when the timer has been determined to not be running, starting the timer and recalculating the delta value.

Alternatively or additionally to any of the embodiments above, the method may further comprise when the timer has been determined to be running, determining whether the timer has expired; when the timer has been determined to have not expired, recalculating the delta value; and when the timer has been determined to have expired, decreasing the pumping rate by a predetermined amount.

Alternatively or additionally to any of the embodiments above, the method may further comprise sensing a measure related to a pressure in the lumen of the fluid line at a location upstream of the pump and the filter module; and shutting down the pump when a value based on the measure related to the pressure in the lumen of the fluid line at a location upstream of the pump and the filter module has reached or gone beyond a predetermined value.

Alternatively or additionally to any of the embodiments above, the method may further comprise sensing a measure related to a pressure in the lumen of the fluid line at a location downstream of the pump and the filter module; and shutting down the pump when a value based on the measure related to the pressure in the lumen of the fluid line at a location downstream of the pump and the filter module has reached or gone beyond a predetermined threshold.

Alternatively or additionally to any of the embodiments above, controlling operation of the pump in an automated manner may include controlling operation of the pump using a control loop that is repeated over time.

A computer readable medium having stored thereon in a non-transitory state a program code for use by a computing device, the program code causing the computing device to execute a method for controlling fluid flow through a cerebrospinal fluid filtering module. The method may comprise: outputting a control signal to a pump to pump cerebrospinal fluid through a filter module via a fluid line;

determining a value based on a measure related to a pressure in a lumen of the fluid line at a location upstream of the filter module; and configuring the control signal to adjust a pumping rate of the pump, wherein the configuring the control signal is based on one or both of the value based on the measure related to a pressure in the lumen of the fluid line at the location upstream of the filter module and a delta value, the delta value is a difference between the value based on the measure related to a pressure in the lumen of the fluid line sensed at a location upstream of the filter module at a time T and the value based on the measure related to a pressure in the lumen of the fluid line sensed at a location upstream of the filter module at a previous time of the time T minus a time interval N.

Alternatively or additionally to any of the embodiments above, configuring the control signal may comprise configuring the control signal according to a first control protocol when the value based on the measure related to a pressure in the lumen of the fluid line at the time T has not reached a threshold; and configuring the control signal according to a second control protocol when the value based on the measure related to a pressure in the lumen of the fluid line at the time T has reached or gone beyond the threshold, the first control protocol is different than the second control protocol.

Alternatively or additionally to any of the embodiments above, the method may further comprise determining in an automated manner the threshold based on the delta value.

Alternatively or additionally to any of the embodiments above, the method may further comprise adjusting the threshold in an automated manner based on a length of continuous time the pump has been operating.

Alternatively or additionally to any of the embodiments above, the threshold may be a first threshold value and configuring the control signal according to the first control protocol may comprise: comparing the value based on the measure related to a pressure in the lumen of the fluid line at the time T to a second threshold value, the second threshold value is based on the delta value; when the value based on the measure related to a pressure in the lumen of the fluid line at the time T has not reached or gone beyond the second threshold value, increasing a pumping rate of the pump by a first predetermined amount; and when the value based on the measure related to a pressure in the lumen of the fluid line at the time T has reached or gone beyond the second threshold value, increasing the pumping rate of the pump by a second predetermined amount.

Alternatively or additionally to any of the embodiments above, the method may further comprise determining in an automated manner the first predetermined amount and the second predetermined amount based on the delta value.

Alternatively or additionally to any of the embodiments above, the method may further comprise: timing in an automated manner with a timer an amount of time the pump has been controlled according to the first control protocol; and stopping timing the amount of time the pump has been controlled according to the first control protocol and recalculating the delta value when increasing the pumping rate of the pump by one of the first predetermined amount and the second predetermined amount and the increase in the pumping rate is equal to or less than zero.

Alternatively or additionally to any of the embodiments above, when the control signal is configured to increase the pumping rate of the pump by one of the first predetermined amount and the second predetermined amount and the increase in the pumping rate is greater than zero, the method may further comprise: determining whether the timer is running; and starting the timer and recalculating the delta value when the timer is determined to be not running.

Alternatively or additionally to any of the embodiments above, the method may further comprise: determining whether the timer has expired; recalculating the delta value when it is determined the timer has expired; and when the timer has expired, configuring the control signal to increase the pumping rate by one of the first predetermined amount and the second predetermined amount based on whether the value based on the measure related to a pressure in the lumen of the fluid line at the time T has or has not reached or gone beyond the second threshold value.

Alternatively or additionally to any of the embodiments above, the timer is a first timer and the method may further comprise: determining whether a second timer is running, the second timer may be configured to time an amount of time the pump has been controlled according to the second control protocol; and starting the second timer and recalculate the delta value when the second timer is determined to be not running.

Alternatively or additionally to any of the embodiments above, the method may further comprise: determining whether the second timer has expired after the second timer has been determined to be running; recalculating the delta value when the second timer has been determined to not have expired; and when the second timer has been determined to have expired, configuring the control signal to decrease the pumping rate by a third predetermined amount.

Alternatively or additionally to any of the embodiments above, the method may further comprise restarting the second timer when second timer has been determined to have expired.

Alternatively or additionally to any of the embodiments above, the method may further comprise recalculating the delta value after restarting the second timer.

Alternatively or additionally to any of the embodiments above, the method may further comprises determining the third predetermined amount based on the delta value.

Alternatively or additionally to any of the embodiments above, the method may further comprise determining the third predetermined amount based on a percentage value of the pumping rate of the pump.

Alternatively or additionally to any of the embodiments above, when the control signal is configured to control operation of the pump according to the second control protocol, the method may further comprise: determining whether a timer is currently timing an amount of time the pump has been controlled according to the second control protocol; and when the timer has been determined to not be running, starting the timer and recalculating the delta value.

Alternatively or additionally to any of the embodiments above, the method may further comprise: when the timer has been determined to be running, determining whether the timer has expired; when the timer has been determined to have not expired, recalculating the delta value; and when the timer has been determined to have expired, configuring the control signal to decrease the pumping rate by a predetermined amount.

Alternatively or additionally to any of the embodiments above, the method may further comprise configuring the control signal to shut down the pump when a value based on a measure related to pressure in the lumen of the fluid line at a location upstream of the pump and the filter module has reached or gone beyond a predetermined value.

Alternatively or additionally to any of the embodiments above, the method may further comprise configuring the control signal to shut down the pump when a value based on a measure related to pressure in the lumen of the fluid line at a location downstream of the pump and the filter module has reached or gone beyond a predetermined threshold.

Alternatively or additionally to any of the embodiments above, controlling operation of the pump in an automated manner may include controlling operation of the pump using a control loop that is repeated over time.

A method of controlling cerebrospinal fluid flow through a cerebrospinal fluid pump/filtration system is disclosed. The method may comprise: pressurizing a fluid line pumping cerebrospinal fluid through the fluid line with a pump at a pumping rate; sensing a measure related to a pressure in a lumen of the fluid line at a location downstream of the pump; determining a rate of pressure decay within the fluid line based on the measure related to a pressure in a lumen of the fluid line that is sensed at a location downstream of the pump; comparing the rate of pressure decay that is determined to a threshold pressure decay; and outputting a control signal when the rate of pressure decay that is determined reaches or exceeds the threshold pressure decay to indicate a leakage in the fluid line.

A method of controlling cerebrospinal fluid flow through a cerebrospinal fluid pump/filtration system is disclosed. The method may comprise: sensing with a first sensor a first measure related to a pressure in a lumen of a fluid line of a cerebrospinal fluid pump/filtration system, the first sensor is located at a first location along the fluid line; sensing with a second sensor a second measure related to the pressure in the lumen of the fluid line, the second sensor is located at a second location along the fluid line; determining a difference between the first measure and the second measure; comparing the difference between the first measure and the second measure to a threshold difference; outputting a control signal indicating a location of a leak or obstruction when the difference between the first measure and the second measure reaches or goes beyond the threshold difference.

A method of flushing a filter module of a cerebrospinal fluid pump/filtration system is disclosed. The method may comprise: pumping fluid through a fluid line of the cerebrospinal fluid pump/filtration system at a pump rate of a pump of the cerebrospinal fluid pump/filtration system; setting a waste pump rate of a waste control mechanism equal to the pump rate of the pump; at a predetermined period of time after setting the waste pump rate of the waste pump mechanism equal to the pump rate of the pump, setting the waste pump rate of the waste control mechanism to a value that is slower than the pump rate of the pump.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 6 is a schematic diagram depicting an example flow control table;

Figure 1:
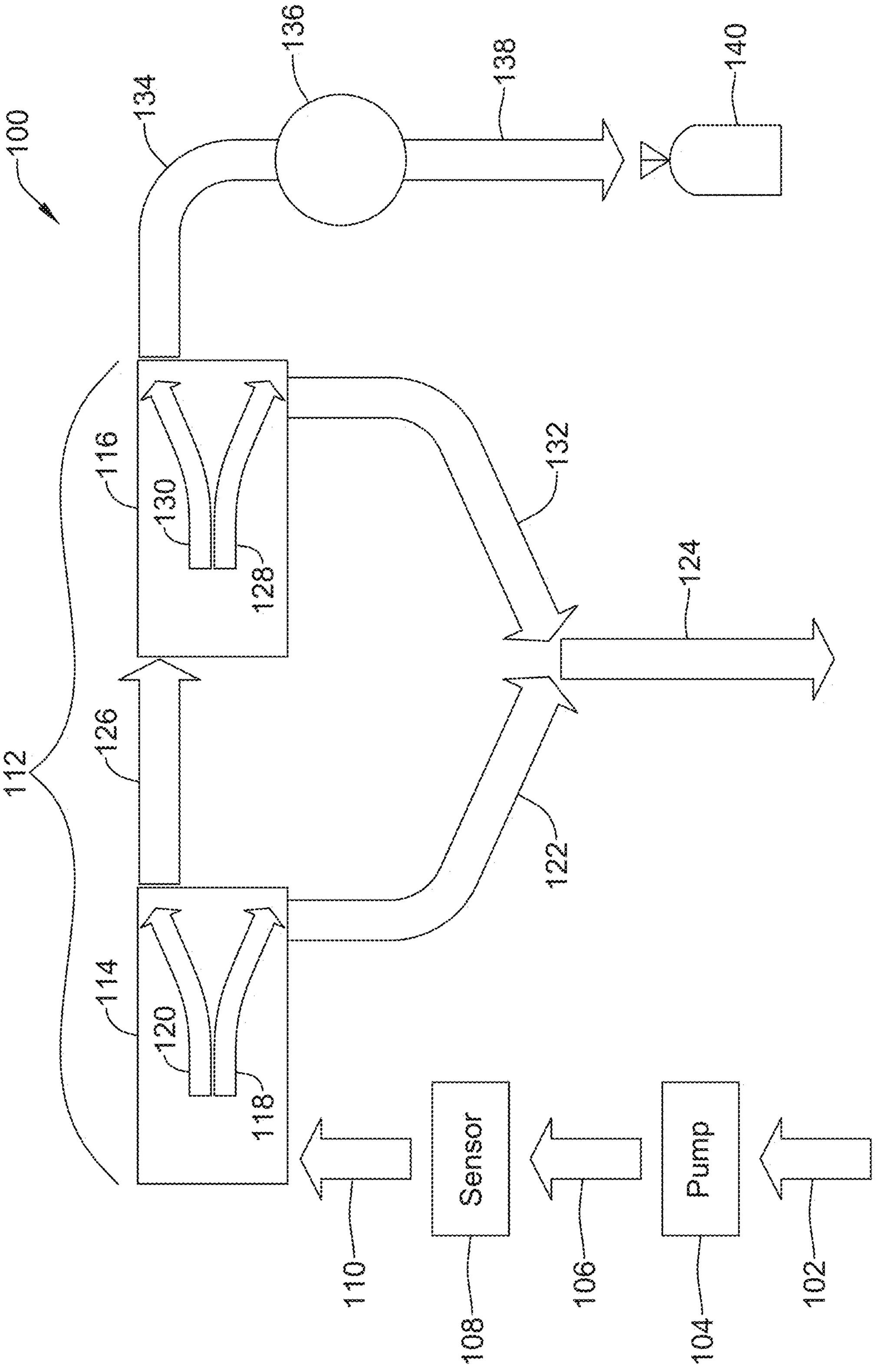
FIG. 1 is a schematic depiction of an example pump/filtration system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAIL DESCRIPTION

Cerebrospinal fluid (CSF) is a generally clear, colorless fluid that is produced in the ventricles, specifically the choroid plexuses, in the brain. The choroid plexus produces approximately 500 milliliters of CSF daily in order to accommodate flushing or recycling of CSF to remove toxins and metabolites, which happens several times per day. From the choroid plexus, CSF flows slowly through a channel (canal) into the space surrounding the brain and spinal column, and then into the body. CSF is found in the space between the pia mater and the arachnoid mater, known as the subarachnoid space. CSF is also found in and around the ventricular system in the brain, which is continuous with the central canal of the spinal cord. In the event of a stroke or other brain trauma, it can be desirable to remove the CSF from one location (e.g., the cervical region of the spine, or a brain ventricle), filter it, and return it to the CSF space at a second location (e.g., the lumbar region of the spine). However, accurate delivery of medical instruments to the CSF space can be challenging.

The present disclosure relates to removal, exchange and recirculation of cerebrospinal fluid (CSF). Devices, systems and methods disclosed herein are used to safely and efficiently navigate the space at and around the brain and spinal cord where the CSF flows through the body, also known as the CSF space. Specialized devices and systems are useful and sometimes necessary to navigate the CSF space due to the difficult points of entry and exit and the potentially life threatening consequences if a mistake is made. Increased safety and efficacy reduce time spent in the surgical suite and potential complications, which improves a patient's recovery from surgery.

Neurapheresis™ therapy and other filtering therapies may result in the removal of materials (e.g., microrganisms, cells, viruses, foreign material, drugs, combinations thereof, and the like) from CSF. These filtering therapies and other therapeutic techniques can be used to treat a number of neurological diseases or conditions, such as Alzheimer's Disease, Parkinson's Disease, Huntington's Disease, Amyotrophic Lateral Sclerosis (ALS), Encephalitis from various causes, Meningitis from various causes, Guillain-Barré Syndrome (GBS), Multiple Sclerosis (MS), HIV-associated neurocognitive disorders, Spinal Cord Injury, Traumatic Brain Injury, cerebral vasospasm, stroke and other diseases or conditions.

The purification, conditioning, and/or compound removal schema or systems (e.g., filtering therapies) can be adjustable to a broad range of biologic parameters and flows. For example, the schema and/or systems can be tailored to a specific disease or group of diseases as suitable, including based on a number of features, such as size, affinity, biochemical properties, temperature, and other features. Purification schema may be based on diffusion, size-exclusion, ex-vivo immunotherapy using immobilized antibodies or antibody fragments, hydrophobic/hydrophilic, anionic/cationic, high/low binding affinity, chelators, anti-bacterial, anti-viral, anti-DNA/RNA/amino acid, enzymatic, and magnetic and/or nanoparticle-based systems.

With regard to a system for use in CSF filtering therapies (e.g., Neurapheresis therapy), the disclosed system can be used to safely and quickly access the CSF space with minimal disturbance to the CSF flow. The systems and devices disclosed herein provide a safe and rapid flow circuit and provide filtration.

The systems and devices disclosed herein can be used to access the CSF space to remove the CSF from one location (e.g., the cervical region of the spine, or a brain ventricle), filter or otherwise treat it, and return it to the CSF space, including at a second location (e.g., the lumbar region of the spine), safely and efficiently. In various aspects, the systems and devices disclosed herein maintain the endogenous intracranial or intraspinal pressure within a physiological range, for example, from about 5 to about 20 mm Hg or from about 0 to about 10 mm Hg or from about −5 to about 10 mm Hg or from about −5 to about 25 mm Hg. The present system thus reduces spinal headache, for example, due to hydrocephalus (abnormal accumulation of CSF in the ventricles of the brain). The present system may also be used to reduce spinal headaches caused by low pressure (e.g., due to over drainage, herniation, etc.). In some aspects, the system may include sensors within the catheter or within the flow circuit to detect clogs or blockages in the system, thereby providing closed loop pressure control. In various aspects, the systems and devices disclosed herein also help the system to perform efficiently by reducing or eliminating recirculating flow loops. The systems and devices maintain spacing between the inlet and outlet, for example, within a range from about 10 cm to about 40 cm. In certain implementations, the spacing is within a range from about 10 cm to about 30 cm. The inlets and outlets are located in places in the CSF space so that turning on a pump or otherwise creating positive or negative pressure in the system will not cause or encourage tissue being drawn into the catheter. In some aspects, the inlets and outlets are placed near the lumbar cervical cisterns to prevent tissue from being drawn into the catheter. In some aspects, there may also be multiple holes along the inlet and outlet for redundancy in case there is tissue blocking some number of holes. In certain implementations, a particular coil pitch of a coiled wire within the catheter may be selected in order to reduce kinking of the catheter. In certain aspects, the inlet-outlet spacing may be selected to be maximized while staying below the level of a cervical region of a patient. In certain aspects, the inlet-outlet spacing may be selected based on vertebral spacing. For example, the spacing may be selected so that the inlet-outlet spacing is within a range of lengths from approximately 5 vertebrae to approximately 12 vertebrae. In certain implementations, a spacing of approximately 10 vertebrae may be selected; however, other configurations (such as those described elsewhere in the specification) may be utilized. When designing such spacing, it may be assumed that a vertebra is approximately 2-3 cm in length, however, other measurements and designs may be used. In certain implementations, a particular size, shape, and/or other configuration of a lumen may be selected to facilitate catheter unblocking and/or the ability of the catheter to resist blockage. For example, a proximal outer diameter of a lumen within a range from approximately 0.060 inches to approximately 0.070 inches and a proximal inner diameter within a range from approximately 0.025 inches to approximately 0.060 inches may be selected; however, other configurations (such as those described elsewhere in the specification) may be utilized.

The disclosed systems and devices are used to access the CSF space and may be used at any access point in the cervical (C1-C7), thoracic (T1-T12), or lumbar region (L1-L5) of the vertebral column. An access site in the cervical region may be used to access the ventricular system in the brain. In one embodiment, the system and device are used to access the lumbar region. In some embodiments, the inlets and outlets are located in places in the spine such that the drainage process will not cause tissue to be drawn into the catheter. For example, when a patient is lying on a table, entry may be made at a suitable angle, such as, for example, about 90 degrees, to access the spine. A traditional catheter must be pushed through a 90 degree bend at the L4-L6 region. The catheters and related delivery devices disclosed herein may be curved such that they can access and navigate this angled bend more easily and efficiently.

Turning to the Figures, FIG. 1 schematically depicts a pump/filtration system 100. The pump/filtration system 100 may have an inlet fluid pathway 102 that may connect to a catheter (e.g., a catheter 200 discussed below with respect to FIG. 3 or other suitable catheter). The pump/filtration system 100 may connect to the catheter directly (e.g., via a connector on the pump/filtration system and/or a connector on the catheter) or through an intermediate tube or mechanism.

A pump 104 may pump fluid (e.g., CSF or other fluid) into, along, and/or through a fluid circuit of the pump/filtration system 100. For example, the pump 104 may pump fluid into an inlet fluid pathway 102 and to a sensor 108 along pathway 106. The pump 104 may be configured to pump CSF through the pump/filtration system 100 with or without additional pumping mechanisms. The CSF traveling through the pump/filtration system 100 may travel along the fluid circuit through various pathways as described herein (e.g., pathways 102, 106, etc.) via a fluid line having a lumen therein (e.g., tubing or other suitable mechanism forming a lumen and configured to facilitate maintaining a desired pressure within the fluid circuit by fluid tight connections at connection points, if any), where the lumen may be configured to facilitate travel of CSF along the fluid circuit from an inlet of the fluid line to the pump 104 and from the pump 104 to an outlet of the fluid line.

The pump 104 may be any suitable type of pump for pumping CSF through the pump/filtration system 100. For example, the pump 104 may be a peristaltic pump or other suitable pump configured to apply a pressure to a fluid line to pump CSF from a patient, through the pump/filtration system 100, and back to the patient. The pump 104 may be a single pump or multiple pumps configured to achieve a desired pressure and/or flow rate within the fluid line. Although the pump 104 is depicted in FIG. 1 as being upstream of a filter module 112, the pump 104 may be entirely or at least partially located at one or more other locations relative to the filter module 112.

The CSF may flow from the pump 104 along the pathway 106 to a sensor 108 downstream of the pump 104. The sensor 108 may be configured to sense a measure within a lumen of a fluid line extending from the pathway 106. Although FIG. 1 depicts the pump/filtration system 100 with a single sensor (e.g., the sensor 108), the pump/filtration system 100 may utilize two sensors, three sensors, or more sensors, as desired, at one or more locations along fluid lines of or traveling through the pump/filtration system 100.

The sensor 108 may be any suitable sensor configured to sense a measure related to a pressure in a lumen of a fluid line between the pathway 106 and a pathway 110. For example, the sensor 108 and/or other sensors described herein as being configured to sense a measure related to pressure may be a pressure sensor, a flow sensor, or other suitable sensor for sensing a measure related to a pressure in the lumen of the fluid line. In one example, the sensor 108 may be a pressure sensor in communication (e.g., direct communication and/or indirect communication, such as through a wall of the of the fluid line) with the lumen of the fluid line and configured to sense a measure related to a pressure in the lumen of the fluid line at a location downstream of the pump 104. Example pressure sensors include any suitable type of pressure sensor element. In one example, the pressure sensor elements may be MEMS (Micro Electro Mechanical Systems) pressure sensor elements such as an absolute pressure sense element, a gauge pressure sense element, or other pressure sense element as desired.

The fluid may flow from the sensor 108 along the pathway 110 to a filter module 112. The filter module 112 may have one or more filters. In one example, the filter module 112 may have a first filter 114 and a second filter 116. In some instances, the first filter 114 and/or the second filter 116 may each be a tangential flow filter (TFF) or other suitable type of filter. For example, the first filter 114 and/or the second filter 116 may include a 5 kDa TFF, a 100 kDa TFF, a 0.2 μm TFF, a 0.45 μm TFF, or the like. Alternatively or in addition, the first filter 114 and/or the second filter 116 may include a dead-end filter (e.g., 5 kDa dead-end filter) and/or an electro-filter (e.g., a filter that excludes materials based on charge).

In at least some instances, the first filter 114 and the second filter 116 may be the same size and/or type (e.g., both the first filter 114 and the second filter 116 may be 100 kDa TFF). In other instances, the first filter 114 and the second filter 116 may differ in size and/or type (e.g., the first filter 114 may be a 5 kDa filter and the second filter 116 may be a 100 kDa TFF filter).

In some instances, the filter module 112 may include only one filter (e.g., the first filter 114). For example, the first filter 114 may be a 5 kDa filter and the first filter 114 may be the only filter. Alternatively, the filter module 112 may include more than two filters (e.g., the first filter 114, the second filter 116, and one or more additional filters).

The first filter 114 may be configured to separate CSF, when CSF is the received fluid, into initial clean CSF 118 (e.g., conditioned CSF) and initial waste CSF 120. As shown in FIG. 1, the initial clean CSF 118 from the first filter 114 may follow a pathway 122 to a clean CSF outlet pathway 124 and the initial waste CSF 120 from the first filter 114 may follow an initial waste CSF pathway 126 to the second filter 116. The clean CSF outlet pathway 124 may connect to an inlet on the catheter or a different catheter connected to the pump/filtration system 100. The connection between the clean CSF outlet pathway 124 may be a direct connection (e.g., via a connector on the pump/filtration system 100 and/or a connector on the catheter) or through an intermediate tube or mechanism.

The second filter 116 may be configured to separate the received initial waste CSF 120 into clean CSF 128 (e.g., conditioned CSF) and waste CSF 130 (e.g. final waste fluid). As shown in FIG. 1, the clean CSF 128 from the second filter 116 may follow a pathway 132 to the clean CSF outlet pathway 124 and the waste CSF 130 from the second filter 116 may follow a pathway 134 to a waste control mechanism 136 (e.g., a manually operated or automated, via a controller, waste pump or other suitable waste control mechanism). The waste control mechanism 136 (e.g., where the waste control mechanism 136 may be or may include a valve, a back pressure valve, a pinch valve, a flow metering mechanism, a pump, etc.) may control a rate at which waste CSF is passed along a waste outlet pathway 138 to a collection apparatus 140 for disposal (e.g., a rate at which the waste CSF is outputted from the filter module 112). The waste control mechanism may be controlled manually and/or in an automated manner.

Figure 2:
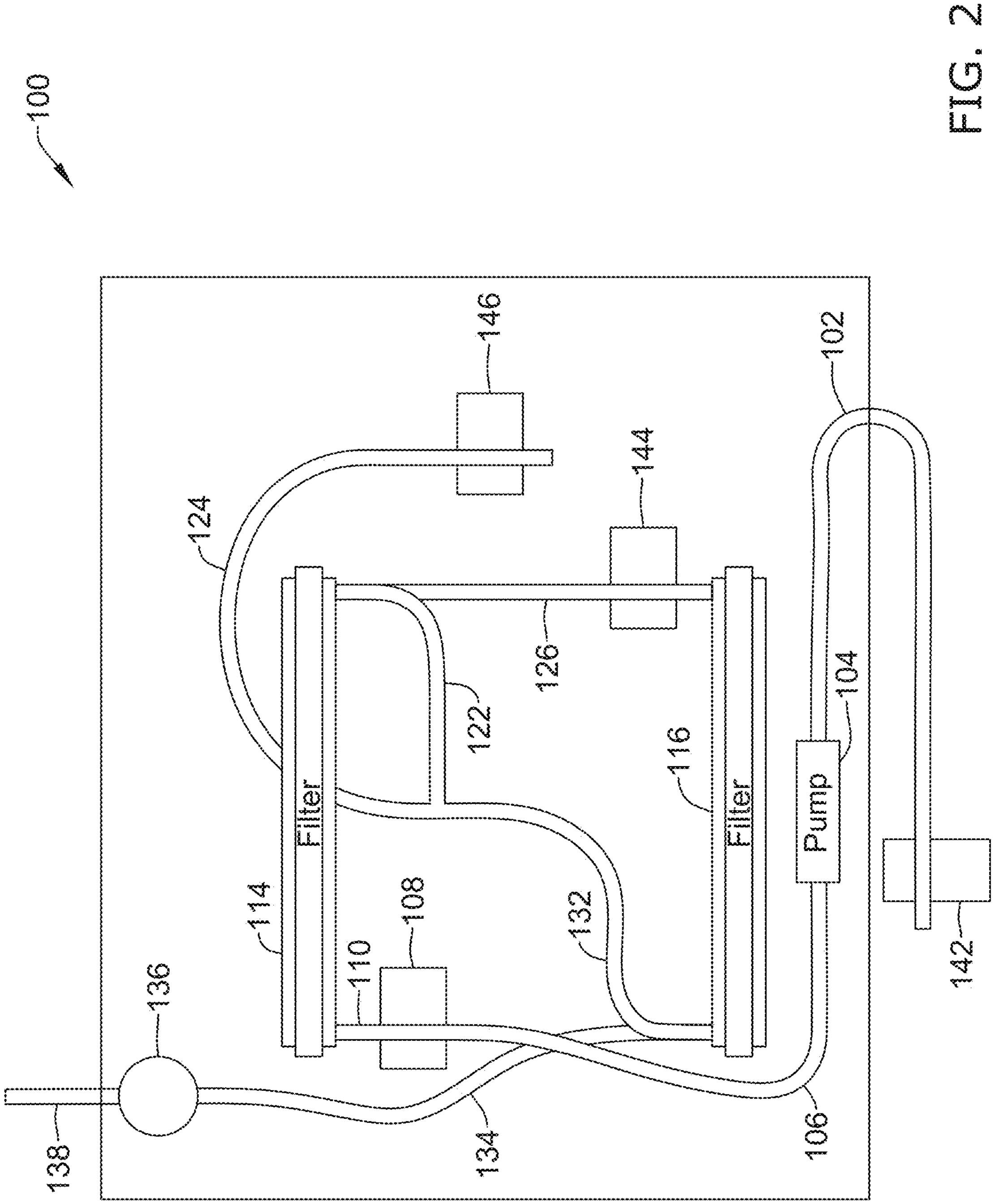
FIG. 2 is a schematic view of an example pump/filtration system.

FIG. 2 depicts a further schematic illustration of the pump/filtration system 100 depicting fluid lines along pathways between components of the pump/filtration system 100 (e.g., pathways 102, 106, 110, 122, 124, 126, 132, 134, 136, 138) to transfer CSF through the pump/filtration system 100. In the pump/filtration system 100 depicted in FIG. 2, four (4) sensors are utilized to facilitate control of the pump/filtration system 100. In the example depicted in FIG. 2, a sensor 142 (e.g., a pressure sensor or other sensor configured to sense a parameter related to pressure) may be located upstream of the pump 104 to sense a measure related to a pump/filtration system inlet pressure in a fluid line at pathway 102, the sensor 108 may be located downstream of the pump 104 and upstream of the first filter 114 to sense a measure related to a first filter inlet pressure in a fluid line adjacent pathways 106, 110, a sensor 144 (e.g., a pressure sensor or other sensor configured to sense a parameter related to pressure) may be located downstream of the first filter 114 and upstream of the second filter 116 to sense a measure related to a second filter inlet pressure in a fluid line adjacent the initial waste CSF pathway 126, and a fourth sensor 146 (e.g., a pressure sensor or other sensor configured to sense a parameter related to pressure) may be located downstream of the second filter 116 to sense a measure related to a pump/filtration system outlet pressure adjacent the clean CSF outlet pathway 124. As discussed in greater detail below, one or more measures from the sensors and/or other sensors of the pump/filtration system 100 may be utilized to control the operation of the pump 104.

Figure 3:
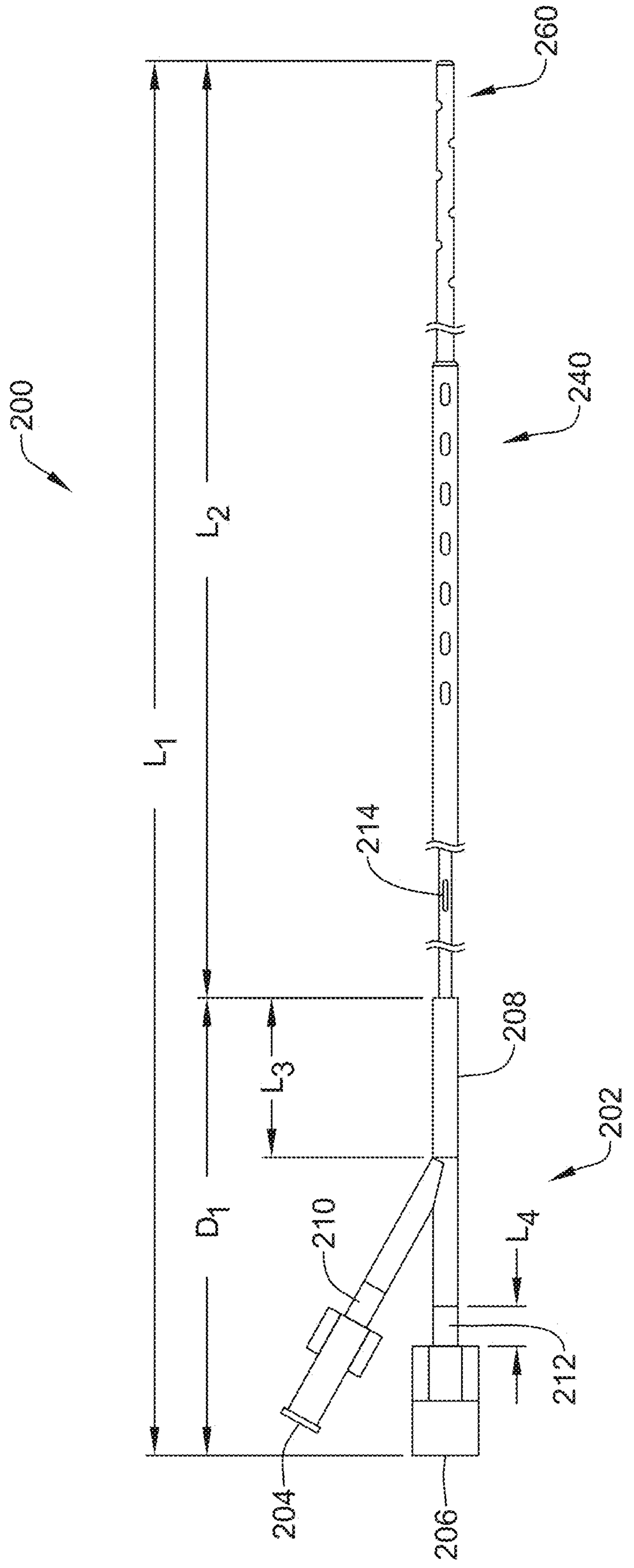
FIG. 3 is a schematic view of an example catheter configured for use with a pump/filtration system.

FIG. 3 illustrates an embodiment of a catheter 200 that may be utilized with the pump/filtration system 100. Although the catheter 200 is described herein, additional descriptions of example catheters that may be used with the pump/filtration system 100 for pumping and/or filtering CSF are described in U.S. Patent Application Ser. No. 62/286,413 filed on Jun. 18, 2018, and titled "SYSTEMS, CATHETERS, AND METHODS FOR TREATING ALONG THE CENTRAL NERVOUS SYSTEM", which is hereby incorporated by reference for all purposes.

FIG. 3 illustrates the catheter 200 having a Y-connector portion 202, a proximal subassembly 240, and a distal subassembly 260. The Y-connector portion 202 may include connectors 204, 206, features 208, 210, 212, a position marker 214, and/or other suitable components. Additionally or alternatively, other catheter configurations may be used with the pump/filtration system 100, as desired.

The connectors 204, 206 may take various forms. For example, as illustrated, the connectors 204, 206 are female and male Luer-lock connectors, respectively, however this is not required. The features 208, 210, 212 may be strain relief and kink resistance features. The feature 208 may be configured to allow flex or deformation of the catheter 200 at portions near a central meeting point of the Y-connector portion 202. The features 210, 212 may be configured to allow flex or deformation of the catheter 200 near the connectors 204, 206. In certain implementations, the features 210, 212 may be color coded to indicate to which lumen of a multi-lumen catheter the connectors 204, 206, may correspond. In certain embodiments, the features 208, 210, 212 may take the form of approximately ⅛" polyolefin heat shrink tubing, but this is not required.

The length $L_1$ of the catheter 200 may be approximately 1,300 mm with a working length $L_2$ of approximately 1,150 mm. The working length $L_2$ may be defined based on various use and design considerations. As illustrated, the working length $L_2$ is the distance from the distal end of the distal subassembly 260 to the distal end of the feature 208. The distance $D_1$ from the distal end of the feature 208 to the proximal end of the connector 206 may be approximately 150 mm. The feature 208 may have a length $L_3$ of approximately 35 mm and the features 210, 212 may have a length $L_4$ of approximately 7 mm. In certain implementations, the catheter 200 may have a length $L_1$ of between approximately 400 mm and approximately 1200 mm, with the working length $L_2$ and other measurements changed accordingly at varying scales.

In use, the catheter 200 may be disposed within the cerebrospinal space (e.g., such as along lumbar cerebrospinal space). CSF may be removed/aspirated using the catheter 200, the pump/filtration system 100, and/or the flow control process 300. The aspirated fluid may be filtered using the pump/filtration system 100 and the flow control process 300 and the filtered/conditioned CSF may be returned to the patient using the catheter 200, the pump/filtration system 100, and the flow control process 300. In some instances, a second catheter 200 (that may be similar in form and function to the catheter 200) may be disposed in a portion of the cranial CNS such as within a ventricle. The second catheter 200 may be used to remove/aspirate cerebrospinal fluid from a cranial region (e.g., a ventricle), condition/filter the cerebrospinal fluid using the pump/filtration system 100, and return the conditioned/filtered cerebrospinal fluid to a region at or adjacent to the cranial region. In some of these and in other instances, the second catheter 200 may be used to infuse a drug (e.g., a chemotherapy drug such as methotrexate) into the cranial region. The catheter 200 (e.g., in the cerebrospinal space) and the second catheter 200 (in the ventricle) may be used together or they may be used alternately. Using a catheter 200 in both the cerebrospinal space and in the ventricle, both for aspiration and of the infusion, may form a cranial-lumbar loop that may improve circulation of cerebrospinal fluid throughout the CNS.

Figure 4:
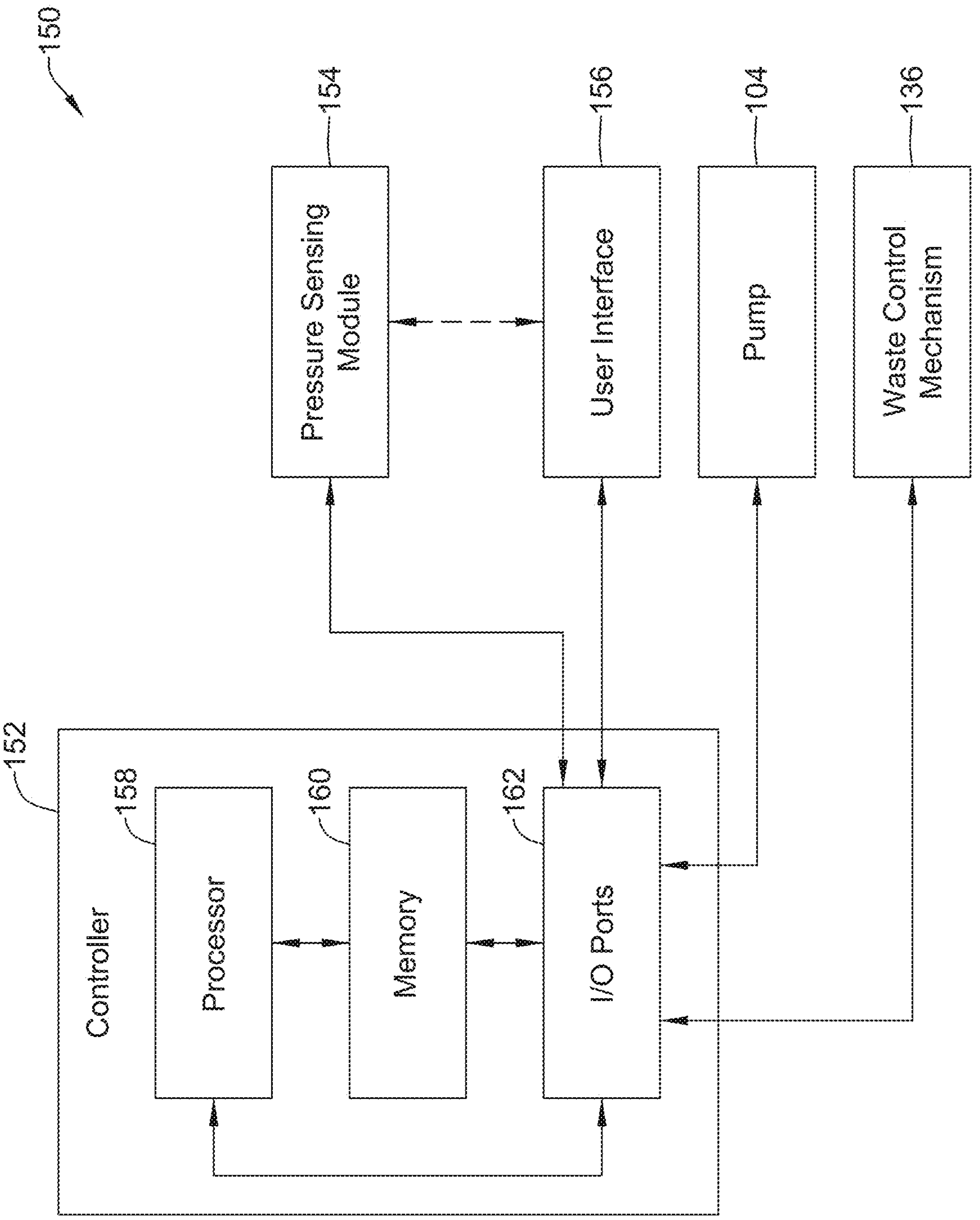
FIG. 4 is a schematic block diagram of an example control system of a pump/filtration system.

FIG. 4 depicts a schematic control system 150 for the pump/filtration system 100. The schematic control system 150 may include a controller 152, the pump 104 in communication with the controller 152, a pressure sensing module 154 in communication with the controller 152, a user interface 156 in communication with the controller 152, and/or one or more other components or systems. In some cases, the pressure sensing module 154 and the user interface 156, when included, may communicate directly with one another, but this is not required.

The controller 152 may include one or more components. In one example, the controller 152 may include a processor 158, memory 160 in communication with the processor 158, input/output (I/O) ports 162 in communication with the processor 158 and/or the memory 160, and/or one or more other suitable components of the control system 150. In some cases, the memory 160 may be or may include non-transitory computer readable medium that may include or may be programed to include software or other instructions to be executed by the processor 158 and facilitate the controller 152 operating in an automated manner to output control signals via the I/O ports 162 to the pump 104 and/or the waste control mechanism 136 based on input received at the I/O ports 162 from the pressure sensing module 154 and/or the user interface 156 for the purposes of optimizing a flow rate through the pump/filtration system 100 while maintaining filter pressures within a desired range and/or for other desired purposes. Additionally or alternatively, controller 152 may be configured to receive information from the pump 104 and/or the waste control mechanism 136 and/or output control signals to the pressure sensing module 154 and/or the user interface 156.

The processor 158 may include a single processor or more than one processor working individually or with one another. Example processor components may include, but are not limited to microprocessors, microcontrollers, multi-core processors, graphical processing units, and/or other suitable processors.

The memory 160 may include a single memory component or more than one memory components working individually or with one another. Example types of memory may include RAM, ROM, EEPROM, FLASH, other volatile or non-volatile memory, or any other suitable memory for the controller 152. The memory 160 may be or may include non-transitory computer readable medium.

The I/O ports 162 may be any type of communication port configured to communicate with the pressure sensing module 154, the user interface 156, the pump 104, the waste control mechanism 136, and/or one or more other components of the pump/filtration system 100. Example I/O port types may include wired ports, wireless ports, radio frequency (RF) ports, Bluetooth ports, Near-Field Communication (NFC) ports, HDMI ports, Ethernet ports, VGA ports, serial ports, parallel ports, component video ports, S-video ports, composite audio/video ports, DVI ports, USB ports, optical ports, and/or other suitable ports.

The pressure sensing module 154 may include one or more of the sensors 108, 142, 144, 146 discussed above and/or other sensors configured to sense a measure related to a pressure in a lumen of a fluid line. In one example, the pressure sensing module 154 may send readings from one or more of the sensors 108, 142, 144, 146 to the controller 152 and the processor 158 may output a control signal to the pump 104 and/or the waste control mechanism 136 based on the received readings.

The user interface 156 may be any suitable type of user interface configured to facilitate a user interacting with the pump/filtration system 100. For example, the user interface 156 may include a work station, a computer, a computing device, a tablet computer, a phone, a display, a keypad, a touch screen, a mouse, and/or one or more other suitable components that facilitate a user interacting with the pump/filtration system 100.

The control system 150 may be configured to send control signals to the waste control mechanism 136 to control operation of the waste control mechanism 136. For example, the control system 150 may utilize a flow control process to optimize a flow rate of fluid through the waste control mechanism 136 to optimize waste removal from the filter module 112. In some cases, the control system 150 may be configured to send a control signal to the waste control mechanism 136 to shut down the waste control mechanism if a value related to a measure received from the pressure sensing module reaches or goes beyond a threshold level.

The control system 150 may be configured to send control signals to the pump 104 to control operation of the pump 104. In some cases, the control system 150 may utilize a flow control process to optimize a pump rate of the pump 104 to maximize fluid flow through the pump/filtration system 100 while accommodating a time varying nature of contaminants (e.g., a consistency or material make-up of CSF may change over time) and keeping a filter pressure (e.g., a filter pressure measured upstream of the filter module 112 or other suitable filter pressure) within desired boundaries. In one example, the control flow utilized by the control system may operate without having a designated optimal pump rate set point for the pump 104 and/or without having an optimal filter pressure set point. As filter pressure may be proportional to the concentration of contaminants in CSF within the filter module 112, not utilizing an optimal filter pressure set point facilitates using the control flow to pump and filter CSF due to the contaminant concentration in CSF varying over time.

The control system 150 may utilize one or more flow control processes that may include a set of instructions saved within the memory 160 and/or other memory and executed by the processor 158 in response to inputs from the pressure sensing module 154 and/or the user interface 156. In some cases, the flow control process of the flow control system 150 may be an automated flow control process that is configured to adjust operation of a pump in real time (e.g., during a therapy) based on inputs from the control system 150 without any or with limited user interaction. In such cases, the flow control may be an automated flow control process.

Figure 5:
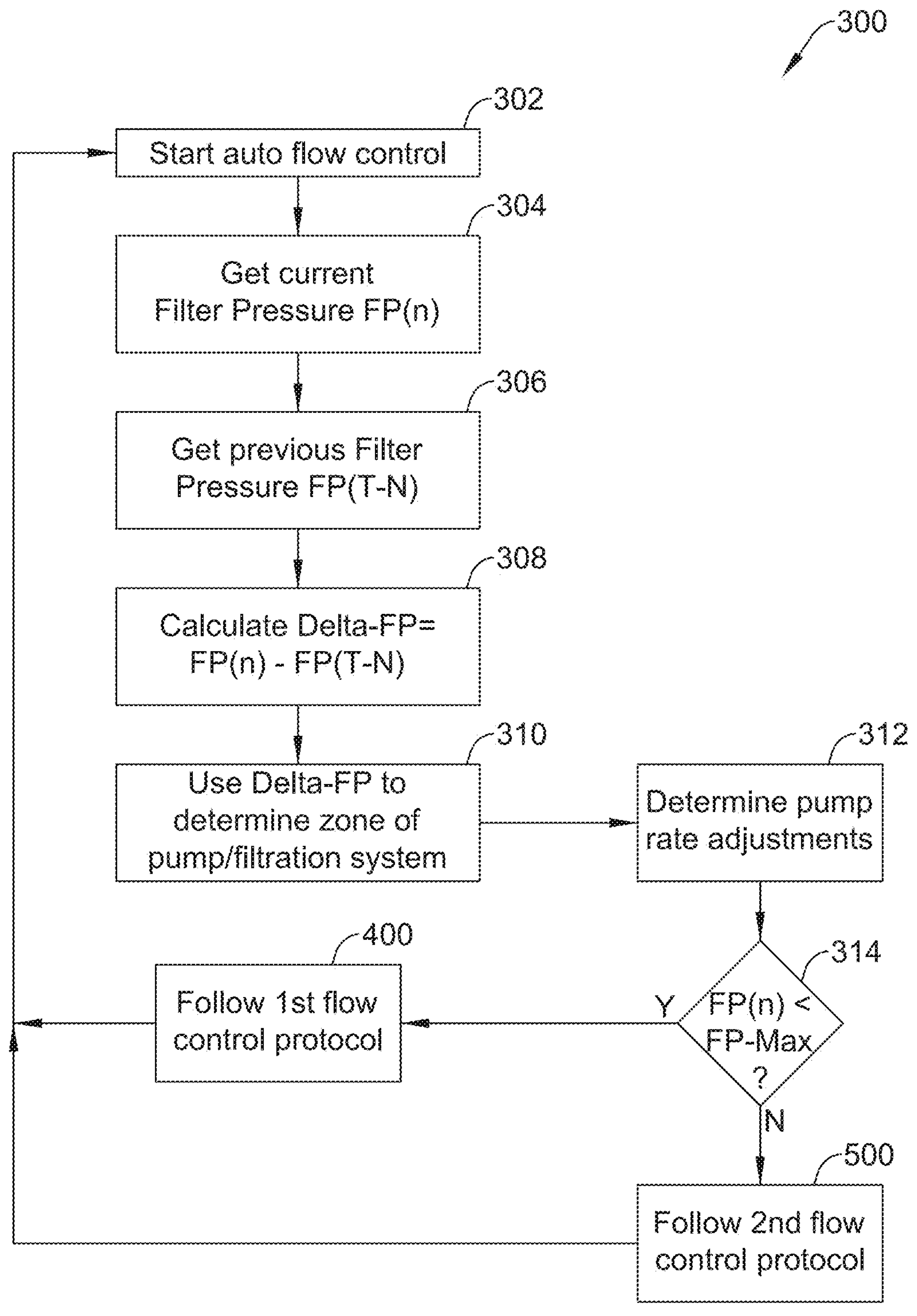
FIG. 5 is a schematic flow diagram of an example flow control process.

FIG. 5 depicts a schematic flow diagram of an illustrative flow control process 300. The flow control process 300 depicted in FIG. 5 may include additional or alternative steps in a similar or different order than what is depicted in FIG. 5, unless expressly indicated otherwise. In some cases, the flow control process 300 may be performed by the controller 150 in an automated manner, where the flow control process 300 may be considered a control loop that is repeated over time. Further, the flow control process 300 may exist substantially entirely in a computer readable medium (e.g., the memory 160, other memory, or other computer readable medium) having instructions (e.g., a control algorithm or other instructions) stored in a non-transitory state thereon that are executable by a processor (e.g., the processor 158 or other processor).

The flow control process 300 may begin with a start 302 of the flow control process 300. Although not discussed in detail herein, the flow control process 300 may include an initiation phase configured to initiate the pump/filtration system 100 and then move to the start 302 of the flow control process 300. Alternatively or in addition, an initiation phase configured to initiate the pump/filtration system 100 may be separate from the flow control process 300.

Once the flow control process 300 has started 302, the flow control process 300 may determine a stability of the pump/filtration system 100 based at least in part on a measure related to a pressure in a fluid line downstream of the pump 104 and passing through the filter module 112.

Although the measure related to a pressure in a fluid line downstream of the pump 104 and passing through the filter module 112 may be a pressure (e.g., a filter pressure) or other measure related to pressure, we will refer to this measure as a filter pressure. Although the filter pressure may be primarily discussed herein as being a measure sensed by the sensor 108 located downstream of the pump 104 and upstream of the filter module 112, the filter pressure may be a value that is or is determined based on measures sensed by one or more alternative or additional sensors of the pump/filtration system.

In some cases, a stability of the pump/filtration system 100 during operation (e.g., during a therapy) may be determined based on the filter pressure. One example technique of determining the stability of the pump/filtration system 100, among other techniques, may be to determine a zone of the pump/filtration system 100 and determine if a filter pressure and/or other measures are within a range specified for the zone. If the filter pressure is below a maximum filter pressure specified by the zone, the pump/filtration system 100 may be considered to be stable and if the filter pressure is above the maximum filter pressure specified by the zone, the pump/filtration system 100 may be considered not stable.

The zone of the pump/filtration system 100 may be determined based on a filter pressure of the filter module 112. The filter pressure may be a pressure related to a measure sensed by a single sensor, a weighted average of pressures related to measures sensed by multiple sensors, a rolling average of pressures related to measures sensed by one or more sensors, and/or other values based on pressures related to measures sensed by one or more sensors. The filter pressure may be sampled, taken, or otherwise determined at a suitable time interval. In some cases, the filter pressure may be sampled at a rate of about 0.5 Hz, about 1.0 Hz, about 1.5 Hz, about 2 Hz, or at one or more other suitable sampling rate. In one example, the filter pressure may be sampled at about 1.0 Hz. Further, the filter pressure may be a rolling average of sampled filter pressures where the filter pressure may be an average of a most recent set number of filter pressures, the most recent filter pressures determined over a set period of time, and/or other suitable rolling average of filter pressures. In one example, the filter pressure may be a one-minute rolling average of pressure based on measures sensed by the sensor 108 of the pump/filtration system 100. Although a one-minute rolling average pressure is referred to, a filter pressure may be an average over a time period that is less than about one-minute or greater than about one-minute.

The zone of the pump/filtration system 100 may be determined in a suitable manner. In one example, the zone of the pump/filtration system 100 may be determined by obtaining 304 a most recent or current filter pressure value based on measures from the pressure sensing module 154 measured at time T and obtaining 306 a filter pressure value from N units of time ago (e.g., at time T minus N). N may be a suitable number of units of time, such that there may be a meaningful change in pressure over that time that is unlikely to be due to noise and/or other non-meaningful contributions to filter pressure in the pump/filtration system 100. For example, N units of time may be set at less than about one (1) minute, about one (1) minute, about two (2) minutes, about three (3) minutes, about four (4) minutes, about five (5) minutes, about six (6) minutes, about ten (10) minutes, greater than about ten (10) minutes or other value in a range from about one (1) to about ten (10) minutes. In one example, N may be five (5) minutes.

After obtaining 304 the filter pressure from N units of time ago, a change in filter pressure (e.g., a delta filter pressure) may be determined or calculated 308. For example, a change in filter pressure may be determined and/or calculated 308 by subtracting the filter pressure from N units of time ago from the current filter pressure FP(n). If a filter pressure decreased over the N units of time, the change in filter pressure may be set to zero (0), but this is not required.

Once a change in pressure has been determined, a zone may be determined by referring to a flow control table, such as a flow control table 350 in FIG. 6 or other table or database and comparing 310 the change in filter pressure to values found in row 352 of the flow control table 350. For example, the row 352 in the flow control table 350 may list ranges of changes in filter pressure that are associated with various zones of the pump/filtration system 100 and the zone of the pump/filtration system 100 may be determined to be the zone that has an associated change in filter pressure range in which the determined change in pressure falls. In the example depicted in FIG. 6, Zone zero (0) may have a range from 0 to five (5) mmHg/5 min (e.g., per N units of time), Zone one (1) may have range from greater than five (5) to ten (10) mm Hg/5 min, Zone two (2) may have a range from greater than ten (10) to twenty (20) mm Hg/5 min, Zone three (3) may have a range from greater than twenty (20) to twenty-five (25) mm Hg/5 min, Zone four (4) may have a range from greater than twenty-five (25) to thirty (30) mm Hg/5 min, and Zone five (5) may have range of all changes in pressure greater than thirty (30) mm Hg/5 min. Although six (6) zones are depicted in FIG. 6 and each zone has a particular range of change in filter pressure values associated therewith, a different number of zones and/or different ranges of changes in filter pressure values associated with the zones may be utilized, as desired. In some cases, zone 0 may be considered a "stable zone", but this is not required.

The flow control table 350 may be saved in the memory 160 of the controller 152 or other memory and accessed by the processor 158. In some cases, the flow control table 350 may be a look-up table, but this is not required. In some case, the flow control table 350 may be in a format other than a table that facilitates associating various zones for the pump/filtration system 100 with various parameters related to the operation of the pump/filtration system 100. Although the flow control table 350 depicts zones associated with control parameters, the flow control table 350 include additional and/or alternative parameters associated with the zones and/or changes in filter pressure or other pressures over time.

Pump rate adjustments to be used in the flow control process 300 may be determined 312 for the determined zone. The pump rate adjustments may be found in rows 358, 360, and 362 of the flow control table 350. For each zone, the row 358 of the flow control table may provide values for a "small increase in pump rate", the row 360 of the flow control table 350 may provide values for a "large increase in pump rate", and the row 362 of the flow control table 350 may provide values for a "decrease in pump rate". In row 358, a small increase in pump rate may be 0.01 ml/min for Zones zero (0) through four (4) and zero (0) ml/min for Zone five (5). In row 360, a large increase in pump rate may be 0.01 ml/min for Zone zero (0) and zero (0) ml/min for Zones one (1) through five (5). In row 362, a decrease in a pump rate may be 0.01 ml/min for Zone zero (0), five percent (5%) of a current pump rate for Zone one (1), ten percent (10%) of a current pump rate for Zone two (2), twenty percent (20%) of a current pump rate for Zone three (3), thirty percent (30%) of a current pump rate for Zone four (4), and fifty percent (50%) of a current pump rate for Zone five (5). Although three (3) different pump rate designations are provided in the example flow control table 350, fewer or more than three (3) pump rate designations may be utilized. Additionally or alternatively, the values in rows 358, 360, 362 may be different than what is depicted in the flow control table 350 of FIG. 6 and/or described herein.

Although table 350 prescribes pump rate adjustments, the flow control process 300 or other processes may be configured to maintain the pump rate of the pump 104 within a minimum pump rate value and a maximum pump rate value. The minimum pump rate value be in a range from about 0.1 milliliters per minute (ml/min) to about 1.0 ml/min or in other suitable ranges of values and the maximum pump rate value may be in a range from about 3.5 mil/min to about 4.5 mil/min or in other suitable ranges of values. In one example, the minimum pump rate value may be about 0.5 ml/min and the maximum pump rate value may be about 4.0 ml/min, but other minimum pump rate values and maximum pump rate values are contemplated.

Once a change in filter pressure and/or a zone has been determined 308, 310, the current filter pressure FP(n) may be compared 314 to a first filter pressure threshold (e.g., a maximum threshold value, such as a maximum filter pressure FP (max)) where the first filter pressure threshold may be associated with a determined 308, 310 change in filter pressure and/or zone and found in row 356 of the flow control table 350. In row 356, a filter pressure maximum value FP(max) (e.g., the first filter pressure threshold value, such as a maximum threshold value) may be 200 mm Hg for Zone zero (0), 190 mm Hg for Zone one (1), 180 mm Hg for Zone two (2), 170 mm Hg for Zone three (3), 160 mmHg for Zone four (4), and 50 mm Hg for Zone five (5). In some cases, the filter pressure maximum value FP (max) in the flow control table 350 may be adjusted over time. In one example, each filter pressure maximum value FP (max) in the flow control table 350 may be increased by fifty (50) mm Hg for each eight (8) hours the pump/filtration system 100 has been in use during a therapy. Additionally or alternatively, the values in rows 356 may be different than what is depicted in the flow control table 350 of FIG. 6 and/or described herein.

If the current filter pressure is less than the first filter pressure threshold associated with the currently identified change in filter pressure and/or zone of the pump/filtration system 100, then a first flow control protocol 400 may be used to control a flow rate of the pump 104. If the current filter pressure FP(n) has reached or gone beyond the filter pressure threshold associated with the currently identified change in filter pressure and/or zone of the pump/filtration system 100, then a second flow control protocol 500 may be used to control a flow rate of the pump 104. After running the one of the first flow control protocol 400 and the second flow control protocol 500, the flow control process 300 may return to the start 302 of the flow control process 300 and create a control loop. In some cases, the first flow control protocol 400 and the second flow control protocol 500 may overlap in scope, but this is not required.

Figure 7:
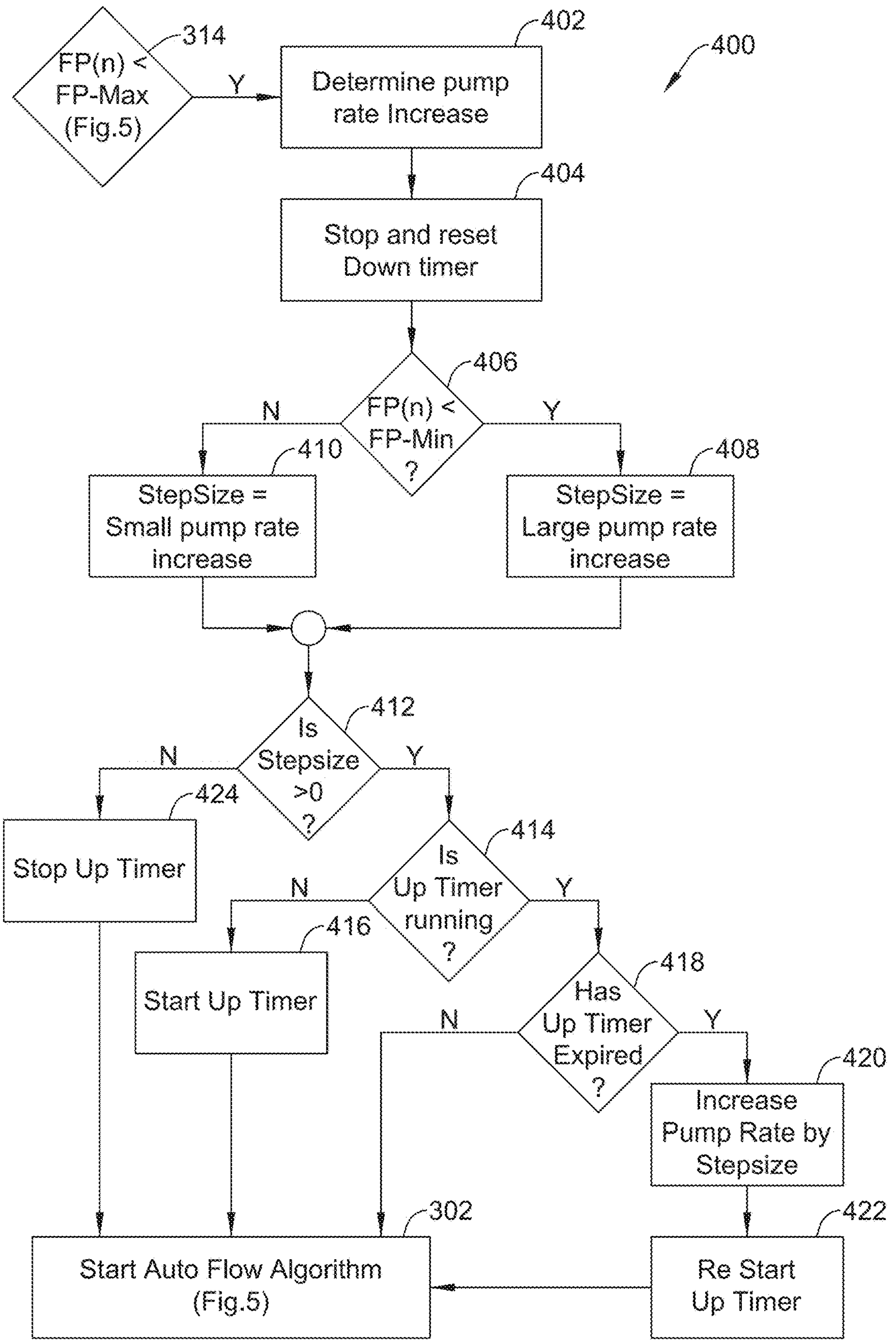
FIG. 7 is a schematic flow diagram of an example first flow control protocol for use in controlling operation of a pump.

FIG. 7 depicts a schematic flow diagram of the first flow control protocol 400. The first flow control protocol 400 depicted in FIG. 7 may include additional or alternative steps in a similar or different order than what is depicted in FIG. 7, unless expressly indicated otherwise.

As depicted in FIG. 7, when the current filter pressure FP(n) is has not reached or gone beyond the first filter pressure threshold for a determined 308, 310 change in filter pressure and/or zone of the pump/filtration system 100, the first flow control protocol 400 may be utilized to control the pump 104 of the pump/filtration system 100. Once the flow control process 300 is following the first flow control protocol 400, possible pump rate increase values for the pump 104 may be determined 402 based on the previously determined 308, 310 change in filter pressure and/or zone in a manner similar to as discussed above with respect to step 312. In one example, if the pump/filtration system 100 has been determined 310 to be operating in Zone 0, the controller 152 may be configured to determine 402 that it is to adjust the pump rate of the pump 104 with either a small pump rate increase 410 of 0.01 ml/min or a large pump rate increase 408 of 0.01 ml/min. If the pump rate increase values for the pump have already been determined (e.g., at step 312 of the flow control process 300), determining 402 the pump rate increases as part of the first flow control protocol 400 may be omitted, but this is not required.

The controller 152 may include a down timer and as part of the first flow control protocol 400, the down timer may be stopped and reset 404 if it has been running. The down timer of the controller 152 may track an amount of time that the filter pressure of the pump/filtration system 100 has reached or gone beyond the first filter pressure threshold (e.g., an amount of continuous or consecutive time the controller 152 has been controlling operation of the pump/filtration system 100 according to the second flow control protocol 500 without controlling operation of the pump/filtration system 100 according to the first flow control protocol 400). As such, as the controller 152 advances to the first flow control protocol 400 in response to a determination 314 that a current filter pressure FP(n) has not reached or gone beyond the first filter pressure threshold, the down timer may be reset and stopped once the controller 152 starts following the first flow control protocol 400.

In some cases, the down timer may be a countdown timer, where the timer may be configured to count down from a predetermined time. For example, the down timer may be configured to count down from thirty (30) seconds, one (1) minute, two (2) minutes, three (3) minutes, five (5) minutes, 10 (ten) minutes or other suitable amount of time. In other instances, the down timer may not be a countdown timer and may start timing from a time of zero (0) units of time. Such a timer may expire, if at all, after a predetermined set of time. In one example, the down timer may be utilized to prevent decreasing the pumping rate faster than desired.

When using the flow control table 350 in FIG. 6, row 366 of the flow control table 350 may provide values of time from after which the down timer may expire for each zone. In row 366, the value of time may be sixty (60) seconds for each zone from Zone zero (0) through Zone four (4) and thirty (30) seconds for Zone five (5). As discussed above, additional or alternative times are contemplated.

When following the first flow control protocol 400, the controller 152 may be configured to determine 406 if the current filter pressure FP(n) has gone beyond a second filter pressure threshold (e.g., a minimum threshold value, such as a filter pressure minimum FP (min)) for a determined 308, 310 change in pressure and/or zone. If the current filter pressure FP(n) has gone beyond the second filter pressure threshold, the controller 152 may output a signal via the I/O ports 162 to the pump 104 to increase 408 a pump rate by a large pump rate increase that was previously determined 402 (and/or 312). If the current filter pressure FP(n) has not gone beyond the second filter pressure threshold, the controller 152 may output a signal via the I/O ports 162 to the pump 104 to increase 410 a pump rate by a small pump rate increase that was previously determined 402 (and/or 312).

The filter pressure minimum FP(min) (e.g., the second filter pressure threshold, such as a minimum threshold value) may be associated with a determined 308, 310 change in filter pressure and/or zone and found in row 354 of the flow control table 350. In row 354, a filter pressure minimum value FP (min) may be fifty (50) mmHg for Zone zero (0) through Zone five (5). Additionally or alternatively, the values in row 354 may be different than what is depicted in the flow control table 350 of FIG. 6 and/or described herein.

After the pump rate of the pump 104 has been adjusted according to one of a small pump rate increase and a large pump rate increase, the controller 152 may determine 412 if the pump rate increase was greater than a pump rate increase threshold. In one example, the pump rate increase threshold may be zero (0), a function of a current pump rate, or other suitable pump rate increase threshold. If the pump rate increase was greater than the pump rate increase threshold, the controller 152 may be configured to determine 414 whether an up timer is running. If the up timer has not been running, the controller 152 may be configured to start 416 the up timer and then start 302 the flow control process 300 again.

The up timer of the controller 152 may track an amount of time that the filter pressure of the pump/filtration system 100 has not reached or gone beyond the first filter pressure threshold (e.g., an amount of continuous or consecutive time the controller 152 has been controlling operation of the pump/filtration system 100 according to the first flow control protocol 400 without controlling operation of the pump/filtration system 100 according to the second flow control protocol 500). In some cases, the up timer may be a countdown timer, where the timer may be configured to count down from a predetermined time. For example, the up timer may be configured to count down from thirty (30) seconds, one (1) minute, two (2) minutes, three (3) minutes, five (5) minutes, 10 (ten) minutes or other suitable amount of time. In one example, the up timer may be utilized to prevent increasing the pumping rate faster than desired. In other instances, the up timer may not be a countdown timer and may start timing from a time of zero (0) units of time. Such a timer may expire, if at all, after a predetermined set of time.

When using the flow control table 350 in FIG. 6, row 364 of the flow control table 350 may provide values of time after which the up timer may expire for each zone. In row 364, the value of time may be sixty (60) seconds for each zone from Zone zero (0) through Zone five (5). As discussed above, additional or alternative times are contemplated.

If the up timer has been running, the controller 152 may then determine 418 whether the up timer has expired. If the up time has not expired, the controller 152 may be configured to start 302 the flow control process 300 again.

If the up timer has expired, the controller 152 may output a control signal via the I/O ports 162 to the pump 104 to increase 420 the pump rate of the pump 104 by either small pump rate increase or the large pump rate increase based on the determination 406 of whether the current filter pressure FP(n) has gone beyond the second filter pressure threshold for the determined 308, 310 change in filter pressure and/or zone, where the pump rate may be adjusted by the large pump rate increase (e.g., a first predetermined amount) when the current filter pressure FP(n) has gone beyond the second filter pressure threshold and adjusted 410 by the small pump rate increase (e.g., a second predetermined amount) when the current filter pressure FP(n) has not gone beyond the second filter pressure threshold. Waiting until the up timer has expired facilitates increasing the pumping rate of the pump 104 at desired intervals. After the controller increases 420 the pump rate of the pump 104, the controller 152 may reset and restart 422 the up timer and then start 302 the flow control process 300 again.

Returning to the determination 412 of whether the pump rate increase is greater than pump rate increase threshold, if the pump rate increase is not greater than the pump rate increase threshold, the controller may be configured to stop 424 the up timer. After stopping 424 the up timer, the controller may then start 302 the flow control process 300 again.

Figure 8:
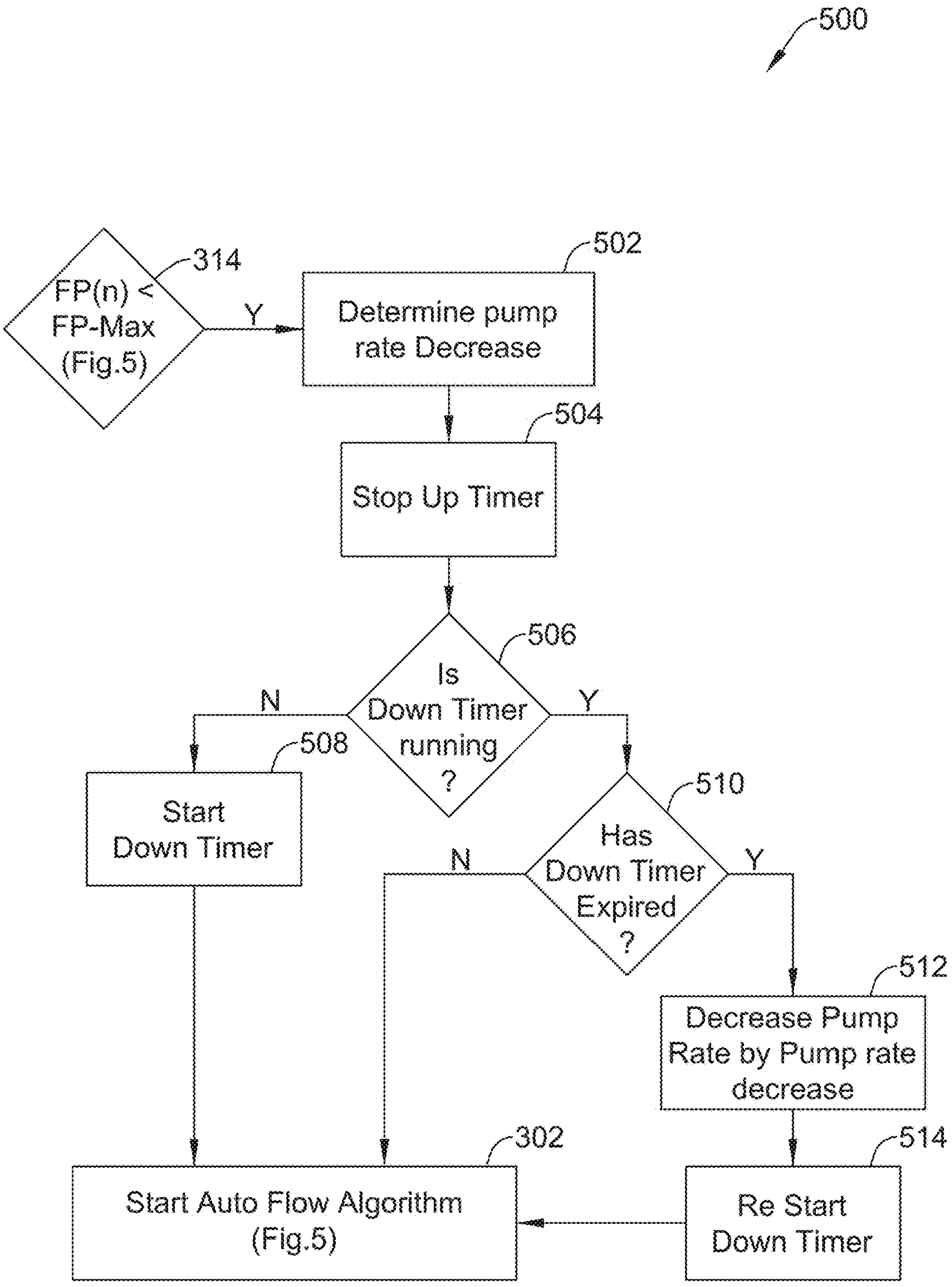
FIG. 8 is a schematic flow diagram of an example second flow control protocol for use in controlling operation of a pump.

FIG. 8 depicts a schematic flow diagram of the second flow control protocol 500. The second flow control protocol 500 depicted in FIG. 8 may include additional or alternative steps in a similar or different order than what is depicted in FIG. 8, unless expressly indicated otherwise.

As depicted in FIG. 8, when the current filter pressure FP(n) has reached or gone beyond the first filter pressure threshold for a determined 308, 310 change in filter pressure and/or zone of the pump/filtration system 100, the second flow control protocol 500 may be utilized to control the pump 104 of the pump/filtration system 100. Once the flow control process 300 is following the second flow control protocol 500, possible pump rate decrease values for the pump 104 may be determined 502 based on the previously determined 308, 310 change in filter pressure and/or zone in a manner similar to as discussed above with respect to step 312. In one example, if the pump/filtration system 100 has been determined 310 to be operating in Zone zero (0), the controller 152 may be configured to determine 502 that it is to decrease the pump rate of the pump 104 by 0.01 ml/min. In another example, if the pump/filtration system 100 has been determined 310 to be operating in Zone two (2), the controller 152 may be configured to determine 502 that it is to decrease the pump rate of the pump 104 by ten percent (10%) of the pump rate at which the pump 104 is currently pumping. If the pump rate decrease values for the pump have already been determined (e.g., at step 312 of the flow control process 300), determining 502 the pump rate decrease as part of the second flow control protocol 500 may be omitted, but this is not required.

As discussed with respect to the first flow control protocol 400, the controller 152 may include the up timer and as part of the second flow control protocol 500, the up timer may be stopped 504 if it has been running. Additionally or alternatively, the controller 152 may be configured to determine 506 if the down timer is running. If the down timer has not been running, the controller 152 may be configured to start 508 the down timer and then start 302 the flow control process 300 again.

If the down timer has been running, the controller 152 may then determine 510 whether the down timer has expired. If the down timer has not expired, the controller 152 may be configured to start 302 the flow control process 300 again.

If the down timer has expired, the controller 152 may output a control signal via the I/O ports 162 to the pump 104 to decrease 512 the pump rate of the pump 104 by the determined 502 decrease in pump rate value. Waiting until the down timer has expired to decrease the pumping rate of the pump 105 may facilitate decreasing the pumping rate of the pump 104 at desired intervals to ensure the pumping rate is not decreased faster desired. After the controller 152 decreases 512 the pump rate of the pump 104, the controller 152 may reset and restart 514 the down timer and then start 302 the flow control process 300 again.

As suggested in the descriptions of the flow control process 300, the first flow control protocol 400, and the second flow control protocol 500, the flow control procedures (e.g., including the flow control process 300, the first flow control protocol 400, the second flow control protocol 500, and/or other flow control procedures) may be repeated in real time. In operation, the flow control process 300 may be constantly running in an automated manner during operation of the pump/filtration system 100 to adjust a pump rate of the pump 104 in response to changing pressures in the fluid line, particularly with respect to the filter module 112. Such a configuration that is response to different concentration of contaminants in CSF and/or conditions of the filter module 112 over time may facilitate optimizing a pumping rate of CSF while maintaining a filter pressure within acceptable limits.

In addition to or as an alternative to the features of the flow control process 300, the controller 152 may take one or more other control actions. For example, the controller 152 may be configured to take one or more safety pump shut down actions, among other actions. In one example, the controller 152 may receive measures from one or more sensors of the pressure sensing module 154 (e.g., from one or more sensors sensing a measures related to a pressure in the lumen of the fluid line at a location upstream of the pump 104 and filter module 112, at a location downstream of the pump 104 and filter module 112, and/or at one or more other suitable location) and if a value based on the receives measure(s) reaches and/or goes beyond a predetermined or threshold value, the controller may be configured to shut down operation of the pump 104, shut down the waste control mechanism 136, and/or take one or more other control actions.

Additionally or alternatively, in a further example, the controller 152 may be configured to monitor received measures from the pressure sensing module 154 to determine patency and/or leaks along the fluid line through the pump/filtration system 100. In one example, once the fluid line is pressurized by the pump 104 and/or the waste control mechanism 136, the controller 152 may determine and monitor a rate of pressure decay within the fluid line, if any, to determine patency and/or leaks of the pump/filtration system 100. The pressure decay may be based on one or more measures received over time from the one or more sensors pressure sensing module 154 that are downstream of the pump 104. In some cases, the controller 152 may compare the determined rate(s) of pressure decay to a threshold pressure decay and if the monitored rate of pressure decay reaches or goes beyond the threshold pressure decay, the controller 152 may take one or more control actions including, but not limited to, initiating an alarm, shutting down operation of one or both of the pump 104 and the waste control mechanism 136, and/or other suitable control actions. The threshold pressure decay may be a predetermined value programmed into the pump/filtration system 100, a function of a measures received from the pressure sensing module 154, and/or may be a value determined in one or more other suitable manners.

Additionally or alternatively, in a further example, the controller 152 may be configured to monitor received measures from the pressure sensing module 154 to determine locations of a potential leak and/or obstruction along the fluid line through the pump/filtration system 100. In one example, measures from two or more sensors (e.g., flow sensors, pressure sensor, etc.), from the pump 104 and at least one sensor, from the waste control mechanism 136 and at least one sensor, and/or from the waste control mechanism 136 and the pump 104 may be monitored and utilized to determine locations of potential leaks or obstructions in the fluid line of the pump/filtration system 100. For example, when measures between two sensors (e.g., such as between a first sensor at a first location along the fluid line and a second sensor at a second location along the fluid line) differ by any amount that exceeds and/or goes beyond an expected amount (e.g., a threshold amount), the controller 152 may determine that there is a leak or obstruction between the two sensors. Similarly, if a measure from a sensor differs by an amount that exceeds and/or goes beyond an expected amount for a pump rate of the pump 104 and/or the waste control mechanism 136, the controller 152 may determine there is a leak or obstruction between the pump 104 and/or the waste control mechanism 136 and the sensor. When the controller 152 identifies a location of a leak or obstruction, the controller 152 may take one or more control actions including, but not limited to, initiating an alarm, shutting down operation of one or both of the pump 104 and the waste control mechanism 136, providing the location to the user interface 156, and/or other suitable control actions.

Additionally or alternatively, in a further example, the controller 152 may be configured to flush the filters of the filter module 112. In one example, the controller 152 may be configured to operate the waste control mechanism 136 at a pump rate that matches a pump rate of the pump 104 pumping CSF through the fluid line so that there is minimal or no tangential flow across the filters of the filter module 112. When there is minimal or no tangential flow across the filters of the filter module 112, relatively large particles filtered from CSF (e.g., particles that are removed from the CSF during filtration and that cannot pass through membranes of the filters) may be brushed away from the filters of the filter module 112 with the flow passing from the pump 104 to the waste control mechanism 136. After a predetermined amount of time with the pump rate of the pump 104 equal to the waste pump rate of the waste control mechanism 136, the controller may reduce the waste pump rate to a value below the pump rate of the pump 104. Such a flushing procedure may be configured to decrease a backpressure of the filters of the filter module caused by particles being unable to cross the membranes of the filters in the filter module 112.

The pump/filtration system 100, the catheter 200, and the flow control process 300 may be used to treat a number of conditions. Some of the contemplated conditions include cancer. For example, Leptomeningeal Metastases (LM) is a condition in which cells from a primary solid or hematological tumor metastasize, invade the subarachnoid space (SAS), and spread throughout the cerebrospinal fluid (CSF), resulting in seeding of the leptomeninges along the surface of the central nervous system (CNS). LM represents a late event of cancer progression and the most frequent symptoms include multiple cranial nerve deficits, motor deficits, altered mental status, headache, and radicular pain. The incidence of LM is estimated at 3-5% of cancer patients and has been increasing, due to longer overall survival in cancer patients. LM presents a difficult challenge in metastatic cancer treatment plans, resulting in a devastating prognosis and median survival of 4 months because of lack of effective access and therapies. Systemic therapy with anticancer drugs including methotrexate (MTX), cytarabine and thiotepa are not as effective due to poor penetration of the blood-brain barrier (BBB). Intrathecal (IT) drug delivery systems, including Ommaya reservoirs, have been associated with longer overall survival; however, they require repeated injections and rely on passive diffusion. Future therapies that target the entire CNS and enhance the distribution of IT drugs could further improve survival. CSF is produced at approximately 20 ml/hr, with a total volume of ~150 ml, resulting in a turnover, on average, of three times per day. The production rate of CSF is independent of intracranial pressure (ICP). As LM can block the outflow paths of CSF, patients are at serious risk of hydrocephalus and elevated ICP. Additionally, the relative isolation of the CSF by the BBB and blood-CSF barriers, presents a unique environment for tumor survival.

The pump/filtration system 100, the catheter 200, and the flow control process 300 may have the ability to rapidly clear a number of CSF pathogens and cells, as well as to enhance drug delivery in the CSF. For example, the pump/filtration system 100, the catheter 200, and the flow control process 300 may be used to improve the LM outcome by 1) enhanced exposure and circulation of specific anticancer agents (MTX delivered through an Ommaya reservoir, through the catheter 200, or both) throughout the SAS, (2) local filtering of CSF to remove cancer-spreading circulating tumor cells (CTCs), (3) control of ICP via CSF drainage, (4) filtration of tumor cells (e.g., living and/or dead tumor cells that may clog the natural reabsorption of the CSF via the arachnoid granulations and lymphatic system). The pump/filtration system 100, the catheter 200, and the flow control process 300 may also be used to reduce the concentration of a drug (e.g., a chemotherapy agent such as methotrexate) in the CSF (e.g., in order to remove excess drug, reduce toxicity, etc.).

As alluded to herein, treatment methods are contemplated that include infusing a chemotherapy agent into the patient. In some instances, the chemotherapy agent is methotrexate. Other chemotherapy agents are contemplated. The chemotherapy agent may be infused into the CNS via an Ommaya reservoir (and/or or a similar device including, for example, a Rickham device) implanted in the ventricles of the patient, as is standard of care in these patients. In addition or in the alternative, the chemotherapy agent may be infused into the patient using the catheter 200. For example, the chemotherapy agent may be added to the clean CSF outlet pathway 124, to one of the ports of the catheter 200, via a separate device disposed agent to the catheter 200, or in another suitable manner. The circulation of CSF by the pump/filtration system 100, the catheter 200, and the flow control process 300 may help to circulate the chemotherapy agent throughout the cerebrospinal space and/or the CNS.

Another contemplated condition that the pump/filtration system 100, the catheter 200, and the flow control process 300 may be used to treat is Amyotrophic Lateral Sclerosis (ALS). For example, the pathology of ALS may be correlated with overstimulation of glutamatergic functions/pathways with a corresponding excitotoxicity, increased calcium levels, and/or the generation of reactive oxygen species. Oxidative stress may be involved in pathological mechanisms of ALS via cell death-related release of pro-oxidative compounds and redox-active iron, mitochondrial dysfunction, inflammation, and excitotoxicity. The catheter 200, pump/filtration system 100, and/or the flow control process 300 may be used to help reduce/clear the CSF of oxidative and/or inflammatory agents (e.g., including free radicals, cytokines, chemokines, white blood cells) such as those correlated with the pathology of ALS. Some examples of materials that may be reduced/removed as part of treating ALS may include one or more of insoluble superoxide dismutase-1 (SOD1), glutamate, neurofilament protein, and anti-GM1 ganglioside antibodies.

In some instances, the oxidative and/or inflammatory agents may carry an electrical charge. Removal of such materials may be enhanced utilizing electrofiltration (e.g., a filter having an electrical charge). Accordingly, in at least some instances, the first filter 114, the second filter 116, both, and/or one or more other filter may include an electrically charged filter (electrofilter). In some of these and in other instances, the first filter 114, the second filter 116, or both may include an immunoaffinity column, a size exclusion column, an anionic exchange column, a cationic exchange column, and a Protein A or Protein G column.

In addition to removing CSF-borne pathological mediators correlated with ALS, the pump/filtration system 100, the catheter 200, and the flow control process 300 may also be used to deliver one or more drugs to the CSF. Such treatments may help further reduce oxidative and/or inflammatory agents. In some instances, the drug may be added to the clean CSF outlet pathway 124 (e.g., the return outlet), to one of the ports of the catheter 200, via a separate device disposed agent to the catheter 200, or in another suitable manner. The circulation of CSF by the pump/filtration system 100, the catheter 200, and the flow control process 300 may help to circulate the drug throughout the cerebrospinal space and/or the CNS. Some example drugs that may be utilized may include riluzole, edaravone, or the like.

Another contemplated condition that the pump/filtration system 100, the catheter 200, and the flow control process 300 may be used to treat is herpes simplex encephalitis (HSE). HSE is known to cause severe neuroinflammation, cerebral edema and hemorrhagic necrosis with resultant increases in intracranial pressure (ICP). While medical management has been standardized, aggressive combined medical and surgical management including decompressive craniectomy and/or temporal lobectomy is often performed due to uncontrolled ICP, neuroinflammation and cerebral edema. The production of reactive oxygen species (ROS) are also believed to be a component of natural defenses to viral infection. However, the lipid-rich environment of the CNS may be susceptible to oxidative damage. Thus, oxidative damage can be correlated with HSE infection.

The pump/filtration system 100, the catheter 200, and the flow control process 300 may be used to remove oxidative and/or inflammatory agents (e.g., including free radicals, cytokines, chemokines, white blood cells) such as those correlated with the pathology of HSE. In some instances, the oxidative and/or inflammatory agents may carry an electrical charge. Removal of such materials may be enhanced utilizing electrofiltration (e.g., a filter having an electrical charge). Accordingly, in at least some instances, the first filter 114, the second filter 116, or both may include an electrically charged filter (electrofilter).

Another contemplated condition that the pump/filtration system 100, the catheter 200, and the flow control process 300 may be used to treat is human immunodeficiency virus (HIV) and/or acquired immune deficiency system (AIDS). HIV infection of the CNS can lead to a number of complications including meningitis, acute inflammatory polyneuropathy (AIDP), immune reconstitution inflammatory syndrome (IRIS)-initiated by introduction of antiretroviral therapy, chronic inflammatory polyneuropathy (CIDP), distal symmetric polyneuropathy (DSP), progressive multifocal leuko-encephalopathy (PML), and HIV-associated neurocognitive disorders (HAND). The pump/filtration system 100, the catheter 200, and the flow control process 300 may be designed to filter/reduce/remove a number of different strains of HIV from the CNS. This can reduce viral load in the CSF and/or reduce complications associated with HIV infection in the CNS. In addition, The pump/filtration system 100, the catheter 200, and the flow control process 300 may be designed to filter/reduce/remove a number of different inflammatory agents associated with HIV from the CNS.

Another contemplated condition that the pump/filtration system 100, the catheter 200, and the flow control process 300 may be used to treat is multiple sclerosis (MS). Two subtypes, Clinically Isolated Syndrome (CIS) and Relapsing-Remitting Multiple Sclerosis (RRMS), represent the disease absent progression, while Primary Progressive (PPMS) and Secondary Progressive (SPMS) represent patients with progressive disease from the start or after RRMS, respectively. Neuroinflammation leading to multifocal lesion formation, demyelination, axonal damage and consequent neurodegeneration are hallmarks of the disease. Current treatments may be classified as including (1) anti-inflammatory naturally-occurring molecules (IFN-beta), (2) molecules that stimulate anti-inflammatory (glatiramer acetate) or inhibit autoreactive (teriflunomide) cell proliferation, (3) immunosuppressive monoclonal antibodies (natalizumab), (4) molecules that bind transcription factors to enhance anti-inflammatory mechanisms or suppress pro-inflammatory ones (dimethyl fumarate), and (5) agents that inhibit egress of lymphocytes from lymphoid tissue to the CNS (fingolomod). In some instances, the pump/filtration system 100, the catheter 200, and the flow control process 300 may be designed to filter/reduce/remove a number of different inflammatory agents associated with MS including immune cells (immunoglobins, neutrophils, lymphocytes, monocytes, and the like), oxidative and/or inflammatory agents (e.g., including free radicals, cytokines, chemokines, white blood cells) such as those correlated with the pathology of MS, and the like. This can help treat MS and/or improve the symptoms thereof.

Another contemplated condition that the pump/filtration system 100, the catheter 200, and the flow control process 300 may be used to treat is Guillain-Barré syndrome (GBS). GBS is the most common cause of acute paralytic neuropathy worldwide. Acute motor axonal neuropathy (AMAN) and acute inflammatory demyelinating polyneuropathy (AIDP) are the main phenotypes. GBS may arise in individuals through a combination of host genetic and environmental factors, and preceding infection by pathogens including *Campylobacter jejuni* and Zika virus. Prevailing mechanisms of action implicate molecular mimicry of foreign antigen and gangliosidic residues resulting in the development of autoantibodies which recognize myelin or axonal components and initiate an inflammatory immune response including macrophage and/or lymphocytic infiltration, complement deposition, and cytokine production. CSF analysis shows elevated protein (>400 mg/L) and the absence of pleocytosis in 90% of patients. Elevated levels of neuroinflammatory cytokines and other proteins involved in the pathology have been noted, though specific immunological protein profiles of GBS CSF are heterogenous. In some of these and in other instances, a second catheter (e.g., which may be similar in form and function to the catheter 200, an Ommaya reservoir, or the like) may be used to infuse a drug into the cranial region.

Current treatments for GBS may include plasma exchange (PE) or intravenous immunoglobulins (IVIg) with supportive care. Based on protein abnormalities of the CSF in GBS patients, including elevated levels of inflammatory cytokines TNF-$\alpha$ and IL-6[7], anti-ganglioside antibodies, and activated complement components, filtration of CSF to reduce/remove inflammatory may help to reduce GBS systems and/or treat GBS. In some instances, the catheter 200, pump/filtration system 100, and/or the flow control process 300 may be designed to filter/reduce/remove a number of different inflammatory agents associated with GBS including immune cells (immunoglobins, neutrophils, lymphocytes, monocytes, and the like), oxidative and/or inflammatory agents (e.g., including free radicals, cytokines, chemokines, white blood cells) such as those correlated with the pathology of GBS, and the like. This can help treat GBS and/or improve the symptoms thereof. In some instances, the pump/filtration system 100, the catheter 200, and the flow control process 300 may include a 5 kDa filter when used for treating GBS. Other filter sizes are contemplated including those disclosed herein. For example, the pump/filtration system 100, the catheter 200, and the flow control process 300 may include a 5 kDa tangential flow filter, a 100 kDa tangential flow filter, an electrofilter, or a combination thereof.

Another contemplated condition that the pump/filtration system 100, the catheter 200, and the flow control process 300 may be used to treat is meningitis. Bacterial meningitis occurs when pathogenic bacteria enter the subarachnoid space and cause a pyogenic inflammatory response. Gram-negative bacterial meningitis (GBM) is a devastating condition that occurs when gram-negative bacteria invade the central nervous system (CNS). There are 30,000 US cases and over 1 million cases of GBM worldwide annually. When bacterial infections are manifested as GBM, it creates an extreme burden of mortality, often exceeding 30%, and morbidity to the patient and is very difficult for clinicians to treat, even when caused by bacteria susceptible to standard antibiotics. It is seen most commonly in children or immunocompromised patients, such as those with HIV, post organ-transplant or post-neurosurgical procedures. Current treatment guidelines include intravenous cephalosporins or carbapenems or polymycin for at least 10 days to 2 weeks. In the presence of gram-negative enteric bacterial meningitis, classically occurring around trauma and neurosurgical procedures, highly resistant bacteria can cause disease. Antibiotics like aminoglycosides and polymycins are considered for treatment but the therapeutic-toxic ratio is poor for these agents with systemic use in CNS disease and there may be no optimal treatments.

Three key gram-negative pathogens that have been deemed critical priority include *Pseudomonas, Acinetobacter* and *Klebsiella* (PAK). These gram-negative bacteria can cause severe and often deadly infections such as pneumonia, bloodstream infections and, specifically, nosocomial meningitis. These bacteria have become resistant to a large number of antibiotics, including carbapenems and third generation cephalosporins—the best available antibiotics for treating multidrug-resistant bacterial meningitis. The world health organization acknowledges that multi-modal approaches are needed and that waiting any longer will cause further public health problems and dramatically impact patient care and survival. This raises the very real possibility of GBM infections that are untreatable by presently available antibiotics. This return to the pre-antibiotic era has unfortunately become a reality in many parts of the world.

Reduction in CSF organism burden is the single most important factor impacting survival and is linked to a better overall clinical outcome. The rapid reduction in CSF organism burden is important, with sterilization of the CSF in the first 24 hours. Optimization of the antibiotic effect depends directly on the organism load that is present and on the direct activity of antibiotic therapy being started early in infection. Determining which antibiotic agent will be most effective is becoming increasingly more difficult in the face of drug-resistant bacteria such as PAK. Clinical data for new antibiotics for bacterial meningitis simply have not kept pace with the rise of resistance, and the development of new therapeutic approaches is urgently needed. Additionally, experimental animal models have shown that outcome from bacterial meningitis are related to the severity of inflammation in the subarachnoid space (SAS) and could potentially be improved by modulation of the inflammatory response.

The pump/filtration system 100, the catheter 200, and the flow control process 300 may provide an innovative new treatment option that provides direct access to the CSF and creates active circulation combined with targeted pathogen removal. This may provide a novel therapeutic approach that rapidly reduces CFUs and CSF bacterial burden and translates to reduced morbidity and mortality from bacterial meningitis.

Accordingly, the present methods provide for ameliorating or reducing the symptoms of bacterial meningitis by reducing or eliminating the presence of one or more of bacterial pathogens and/or their associated endotoxins and/or cytokines in the CSF using the pump/filtration system 100, the catheter 200, and the flow control process 300. The methods comprise removing CSF from a patient, removing at least one of the bacterial pathogens, and/or endotoxins associated with the bacterial pathogens, and/or cytokines from the CSF, and returning the endogenous CSF to the patient, wherein the removing and returning steps are performed concurrently during at least a portion of the treatment. In some embodiments, the cytokines are selected from the group consisting of IL-1ra, IL-6, TNF, CRP, and CXCL10, or combinations thereof.

In some of these and in other instances, the methods provide for ameliorating or reducing the symptoms of bacterial meningitis by introducing the catheter 200 through a spinal access site into a spinal CSF space of a patient, advancing the catheter 200 through the spinal CSF space toward the brain so that the openings of the catheter 200 are disposed within the CSF space and spaced-apart by a preselected distance or adjusted to an appropriate distance, withdrawing CSF through at least some of the openings in the catheter 200, removing at least one of bacterial pathogens and/or their associated endotoxins and/or cytokines from the withdrawn CSF with the pump/filtration system 100 and flow control process 300 (thereby conditioning the CSF), and returning the conditioned CSF through the other of the openings in the catheter 200.

Fungal meningitis (FM) is an infection of the meninges of the central nervous system that manifests from the dissemination of any major fungal pathogen into the subarachnoid space (SAS) via the cerebrospinal fluid (CSF). Cryptococcal Meningitis (CM) is caused by *Cryptococcus neoformans* and is the most common cause of fungal meningitis in adults. Other agents causative of fungal meningitis include: *C. gattii, Blastomyces, Histoplasma, Coccidioides*. Treatment for CM is based on an induction, consolidation, and maintenance approach with antifungals and is well defined elsewhere, but is associated with continued high morbidity and mortality. Drug discovery programs are limited by poor penetration of the Blood Brain Barrier (BBB). Because of this, we developed an alternative catheter-based extracorporeal filtration system (Neurapheresis Therapy) for the filtration of infected CSF. Here we describe the in vitro characterization of Neurapheresis Therapy as an alternative mechanical intervention for filtration of *C. neoformans* cells, polysaccharide antigen, and inflammatory mediators from infected CSF.

The pump/filtration system 100, the catheter 200, and the flow control process 300 may provide an innovative new treatment option that provides direct access to the CSF and creates active circulation combined with targeted pathogen removal. This may provide a novel therapeutic approach that rapidly reduces CFUs and CSF fungal burden and translates to reduced morbidity and mortality from fungal meningitis.

In at least some instances, the pump/filtration system 100 and the catheter 200 may include one or more filters (e.g., the filters 114/116) designed to exclude the passage of fungi therethrough such as *C. neoformans*. In some of these and in other instances, the pump/filtration system 100 and the catheter 200 may include one or more filters (e.g., the filters 114/116) designed to exclude fungi (e.g., *C. neoformans*), associated antigens, and/or inflammatory agents. In at least some instances, a single pass of CSF through a 5 kDa TFF and/or a 100 kDa TFF may be sufficient to exclude *C. neoformans* or other reduce the CFUs of *C. neoformans* in the CSF. In addition, a 5 kDa TFF and/or a 100 kDa TFF may be sufficient to exclude or otherwise reduce *C. neoformans* antigen from the CSF. Furthermore, a 5 kDa and/or 100 kDa TFF may also exclude a number of neuroinflammatory agents such as IL-1ra, IL-6, TNF, CRP, and/or CXCL 10/IP-10 from the CSF.

Accordingly, the present methods provide for ameliorating or reducing the symptoms of fungal meningitis by reducing or eliminating the presence of one or more of fungal pathogens and/or their associated antigens (e.g., Cryptococcal antigen) and/or cytokines in the CSF using the pump/filtration system 100, the catheter 200, and the flow control process 300. The methods comprise removing CSF from a patient, as described herein; removing at least one of the fungal pathogens, and/or antigens associated with the fungal pathogens, and/or cytokines from the CSF, and returning the endogenous CSF to the patient, wherein the removing and returning steps are performed concurrently during at least a portion of the treatment. In some embodiments, the cytokines are selected from the group consisting of IL-1ra, IL-6, TNF, CRP, and CXCL10, or combinations thereof. The fungus/fungi and/or antigens and/or cytokines can be removed from the CSF using one or more filtration system. A 5 kDa and/or 100 kDa TFF may also exclude a number of neuroinflammatory agents such as IL-1ra, IL-6, TNF, CRP, and/or CXCL 10/IP-10.

In some of these and in other instances, the methods provide for ameliorating or reducing the symptoms of fungal meningitis by introducing the catheter 200 through a spinal access site into a spinal CSF space of a patient, advancing the catheter 200 through the spinal CSF space toward the brain so that the openings of the catheter 200 are disposed within the CSF space and spaced-apart by a preselected distance or adjusted to an appropriate distance, withdrawing CSF through at least some of the openings in the catheter 200, removing at least one of fungal pathogens and/or their associated antigens and/or cytokines from the withdrawn CSF with the pump/filtration system 100 and the flow control process 300 (thereby conditioning the CSF), and returning the conditioned CSF through the other of the openings in the catheter 200.

In at least some instances, the pump/filtration system 100, the catheter 200, and the flow control process 300 may be used to deliver drugs to portions of the CNS. For example, some treatments for CM may include the administration of intravenous and oral antifungals such as amphotericin B (AmB) and flucytosine. Generally, intrathecal (IT) AmB boluses may be associated with neurotoxic drug concentrations near the injection site. The use of the pump/filtration system 100, the catheter 200, and the flow control process 300 may allow for the IT infusion of AmB and/or other drugs. Unexpectedly, the pump/filtration system 100, the catheter 200, and the flow control process 300 may also be used to reduce, filter (e.g., with the first filter 114, the second filter 116, or both), or otherwise remove some drugs such as AmB. Because of this, the dosage of AmB can be precisely titrated to a desired dose. If levels of AmB reach undesired levels (e.g., undesired high levels), the pump/filtration system 100, the catheter 200, and the flow control process 300 can be used to quickly remove unwanted quantities of AmB from the CSF.

The pump/filtration system 100, the catheter 200, and the flow control process 300 can also be used to deliver a number of other drugs including drugs where the difference between therapeutic doses and toxic doses are relatively small. For example, a drug may be infused into the CSF using the pump/filtration system 100, the catheter 200, and the flow control process 300. If signs of toxicity are observed or if measurements of the drug concentration in the CSF is higher than desired, the pump/filtration system 100, the catheter 200, and the flow control process 300 can be used to rapidly remove the drug from the CSF. Thus, the pump/filtration system 100, the catheter 200, and the flow control process 300 can be used for controlled delivery of drugs into the CSF of patients and the rapid removal of drugs from the CSF, as desired.

The pump/filtration system 100, the catheter 200, and the flow control process 300 may also help to reduce ICP associated with a number of conditions. For example, some conditions (e.g., such as cancer, HSE, and others) may be associated with higher ICP due to cells (e.g., tumor cells, etc.), inflammatory agents, and the like blocking, clogging, or otherwise impacting natural pathways for reabsorption of CSF. By using the pump/filtration system 100, the catheter 200, and the flow control process 300, materials that might blocking natural reabsorption pathways can be removed/reduced, thereby desirably impacting the volume of CSF and reducing ICP.

Systems are also contemplated that utilize a first port for providing access to the cerebrospinal space and/or the CNS at a first location and a second port for providing access the cerebrospinal space and/or the CNS at a second location. Such ports may be implanted acutely or for extended periods of time. In some instances, the ports may allow for infusion of substances to the cerebrospinal space and/or the CNS, removal of substances from the cerebrospinal space and/or the CNS, or both. One or both of the ports may be or otherwise be similar to an Ommaya reservoir. The ports may be designed to be used with a tube/catheter, the pump/filtration system 100, the catheter 200, and the flow control process 300. For example, a first tube and/or first catheter 200 may be connected with or otherwise be connectable to one of the ports and a second tube and/or second catheter 200 may be connected with or otherwise be connectable to the other port. CSF may be removed from the patient (e.g., using a tube, either the first or the second catheter 200, or the like) and filtered by the pump/filtration system 100 using the flow control process 300. In some instances, the filtered CSF may be returned to the patient using the same tube/catheter. In other instances, the filtered CSF may be returned to the patient using the other tube/catheter. In other words, CSF may be removed from the patient using a catheter at the first port, filtered, and then returned to the patient using a catheter at the second port. This may form a loop-like pathway the helps to circulate CSF through the cerebrospinal space and/or the CNS. The ports may be positioned along the patient in a manner that helps to facilitate circulation of CSF. For example, one of the ports may be positioned at the cranium of the patient (e.g., which may include providing access to the ventricles of the brain) and the other may be positioned along a lumbar region of the spine (e.g., which may provide access to the cerebrospinal space at a position adjacent to the lumbar space). Other locations are contemplated.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It should be noted that delivery sheath and delivery catheter may be used interchangeably for purposes of this description. The exemplary drawings are for purposes of illustration only and the dimensions, positions, order and relative sizes reflected in the drawings attached hereto may vary.

U.S. Patent Application Pub. No. US 2016/0051801 is incorporated herein by reference. U.S. Pat. No. 8,435,204 is incorporated herein by reference. U.S. Patent Application No. 62/568,412 is incorporated herein by reference. U.S. Patent Application No. 62/598,846 is incorporated herein by reference.

The above specification, examples and data provide a complete description of the structure and use of exemplary embodiments of the disclosure as claimed below. Although various embodiments of the disclosure as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure.

What is claimed is:

1. A cerebrospinal fluid flow control system, the system comprising:
- a pump configured to pump cerebrospinal fluid along a fluid circuit;
- a fluid pathway in communication with the pump, the fluid pathway extending along an inlet configured to receive cerebrospinal fluid from a patient, an outlet configured to provide cerebrospinal fluid to the patient, and a lumen configured to facilitate travel of cerebrospinal fluid along the fluid circuit from the inlet of the fluid pathway to the pump and from the pump to the outlet of the fluid pathway;
- a sensor in communication with the lumen of the fluid pathway, the sensor is configured to sense a measure related to a pressure in the lumen of the fluid pathway at a location downstream of the pump;
- a controller in communication with the sensor and the pump; and
- wherein the controller is configured to:
  - determine a threshold value, wherein the threshold value is variable; and
  - control operation of the pump based on a comparison of the measure sensed by the sensor to the threshold value.

2. The system of claim 1, wherein the controller is configured to control operation of the pump based on a delta value based on the measure sensed by the sensor, the delta value is a difference between a value based on the measure sensed by the sensor at a time T and a value based on the measure sensed by the sensor at a previous time of the time T minus a time interval N.

3. The system of claim 2, wherein the controller is configured to determine the threshold value based on the delta value.

4. The system of one of claim 2, wherein the controller is configured to control operation of the pump according to:
- a first control protocol when the value based on the measure sensed by the sensor at time T has not reached the threshold value; and
- a second control protocol when the value based on the measure sensed by the sensor at time T has reached or gone beyond the threshold value, the second control protocol is different than the first control protocol.

5. The system of claim 4, further comprising:
- a timer;
- wherein:
  - when controlling operation of the pump according to the second control protocol, the timer is configured to time an amount of time the controller has been controlling operation of the pump according to the second control protocol;
  - the controller determines whether the timer is running; and
  - when the controller determines the timer is not running, the controller is configured to start the timer and recalculate the delta value.

6. The system of claim 1, wherein the controller is configured to determine the threshold value based on the measure sensed by the sensor.

7. The system of claim 1, wherein the controller is configured to adjust the threshold value based on a length of continuous time the pump has been operating.

8. The system of claim 1, further comprising:
- a filter module configured to receive cerebrospinal fluid from the lumen at a location downstream of the sensor.

9. The system of claim 8, wherein the filter module comprises:
- a first filter configured to output a first output of conditioned cerebrospinal fluid and output initial waste fluid; and
- a second filter downstream of the first filter, the second filter configured to receive the initial waste fluid, output a second output of conditioned cerebrospinal fluid, and output a final waste fluid.

10. The system of claim 8, further comprising:
- a waste pump in communication with the fluid pathway and located downstream of the filter module; and
- wherein the waste pump is configured to at least partially control a waste pumping rate at which waste fluid is outputted from the filter module.

11. A method of controlling cerebrospinal fluid flow through a cerebrospinal fluid module, the method comprising:
- pumping cerebrospinal fluid through a fluid pathway with a pump at a pumping rate, the fluid pathway extending along an inlet configured to receive cerebrospinal fluid from a patient, an outlet configured to provide cerebrospinal fluid to the patient, and a lumen configured to facilitate travel of cerebrospinal fluid from the inlet to the outlet;

sensing a measure related to a pressure in the lumen;

determining a threshold value, wherein the threshold value is variable; and controlling operation of the pump in an automated manner based on a comparison of the threshold value to a value based on the measure related to a pressure in the lumen.

12. The method of claim 11, wherein determining the threshold value is based on the measure sensed.

13. The method of claim 11, further comprising:

adjusting the threshold value based on a length of continuous time the pump has been operating.

14. The method of claim 11, further comprising:

calculating a delta value, the delta value is a difference between a value based on the measure related to a pressure in the lumen at a time T and the value based on the measure related to a pressure in the lumen at a previous time of the time T minus a time interval N; and wherein determining the threshold value comprises determining, in an automated manner, the threshold value based on the delta value.

15. The method of claim 14, wherein controlling operation of the pump in an automated matter comprises:

controlling operation of the pump according to a first control protocol when the value based on the measure related to a pressure in the lumen at the time T has not reached the threshold value; and controlling operation of the pump according to a second control protocol when the value based on the measure related to a pressure in the lumen at the time T has reached or gone beyond the threshold value, the first control protocol is different than the second control protocol.

16. A non-transitory computer readable medium having stored thereon a program code for use by a computing device, the program code causing the computing device to execute a method for controlling fluid flow through a cerebrospinal fluid module comprising:

outputting a control signal to a pump to pump cerebrospinal fluid through along a fluid pathway;

determining a value based on a measure related to a pressure in a lumen along the fluid pathway;

determining in an automated manner a threshold value, wherein the threshold value is variable; and configuring the control signal to adjust a pumping rate of the pump, wherein the configuring the control signal is based on a comparison of the threshold value to the value based on the measure related to the pressure in the lumen along the fluid pathway.

17. The non-transitory computer readable medium of claim 16, wherein determining the threshold value is based on the measure related to the pressure in the lumen along the fluid pathway.

18. The non-transitory computer readable medium of claim 16, wherein the method further comprises:

adjusting the threshold value in an automated manner based on a length of continuous time the pump has been operating.

19. The non-transitory computer readable medium of claim 16, wherein the method further comprises:

calculating a delta value, the delta value is a difference between the value based on the measure related to a pressure in the lumen at a time T and the value based on the measure related to a pressure in the lumen at a previous time of the time T minus a time interval N; and wherein determining the threshold value comprises determining, in an automated manner, the threshold value based on the delta value.

20. The non-transitory computer readable medium of claim 16, wherein controlling operation of the pump in an automated manner includes controlling operation of the pump using a control loop that is repeated over time.

* * * * *